United States Patent [19]
Martinson et al.

[11] Patent Number: 5,811,061
[45] Date of Patent: Sep. 22, 1998

[54] METHOD AND DEVICE FOR TESTING BLOOD UNITS FOR VIRAL CONTAMINATION

[75] Inventors: Jeffrey Martinson, Mundelein; William Bratten, Lake Villa; Li Ming Wang, Vernon Hills; John Chapman, Lake Villa, all of Ill.

[73] Assignee: Baxter International Inc., Deerfield, Ill.

[21] Appl. No.: 686,459

[22] Filed: Jul. 25, 1996

Related U.S. Application Data

[60] Continuation of Ser. No. 434,694, May 4, 1995, abandoned, which is a division of Ser. No. 164,517, Dec. 9, 1993, Pat. No. 5,686,238, which is a continuation-in-part of Ser. No. 37,525, Mar. 24, 1993, Pat. No. 5,498,520, which is a continuation of Ser. No. 833,285, Feb. 10, 1992, abandoned.

[51] Int. Cl.$^6$ ........................................ B01L 3/00
[52] U.S. Cl. ............................ 122/102; 422/99; 422/100; 422/101
[58] Field of Search ...................... 422/100, 102, 422/101; 604/186, 187, 208, 210; 141/13, 2, 27, 115, 365, 366

[56] References Cited

U.S. PATENT DOCUMENTS

| | | | |
|---|---|---|---|
| 1,831,668 | 11/1931 | Juhl | 604/186 |
| 2,648,334 | 8/1953 | Brown et al. | 604/208 |
| 2,856,925 | 10/1958 | Helmer et al. | 604/210 |
| 2,869,541 | 1/1959 | Helmer et al. | 604/210 |
| 3,563,240 | 2/1971 | Silver | 604/87 |
| 3,648,927 | 3/1972 | Abbe et al. | 233/26 |
| 3,770,026 | 11/1973 | Isenberg | 141/2 |
| 4,073,321 | 2/1978 | Moscowitz | 604/208 |
| 4,153,056 | 5/1979 | Silver et al. | 604/211 |
| 4,246,898 | 1/1981 | Travalent et al. | 604/210 |
| 4,275,729 | 6/1981 | Silver et al. | 604/211 |
| 4,642,102 | 2/1987 | Ohmori | 604/210 |
| 4,828,716 | 5/1989 | McEwen et al. | 422/102 |
| 4,874,385 | 10/1989 | Moran et al. | 604/208 |
| 5,084,017 | 1/1992 | Malletone | 604/110 |
| 5,246,011 | 9/1993 | Caillouette | 604/187 |
| 5,263,934 | 11/1993 | Haak | 604/208 |
| 5,342,753 | 8/1994 | Smith, Jr. | |
| 5,344,409 | 9/1994 | Ennis, III et al. | 604/187 |
| 5,385,558 | 1/1995 | Cottone, Sr. et al. | 604/208 |

OTHER PUBLICATIONS

Webster's II, The Riverside Publishing Company, pp. 1094 and 1122, 1994.

Barbara, John A.J. et al. "Polymerase Chain Reaction and Transfusion Microbiology" on *Vox Sang* 1993: 64: pp. 73–81. 1993.

Bøyum, Arne. "Separation of Lymphocytes, Granulocytes, and Monocytes from Human Blood Using Iodinated Density Gradient Media" *Methods in Enzymology*, vol. 108, 1984, pp. 88–102. 1986.

Bruisten, S.M. et al. "Efficiency of White Cell Filtration and a Freeze–Thaw Procedure for Removal of HIV–Infected Cells From Blood" in *Transfusion*, vol. 30, No. 9, 1990, pp. 833–837. 1990.

(List continued on next page.)

*Primary Examiner*—Jill Warden
*Assistant Examiner*—Alexander Markoff
*Attorney, Agent, or Firm*—Robert M. Barrett; Denise M. Serewicz; Bradford R. L. Price

[57] ABSTRACT

A method and apparatus for creating a leukocyte rich sample from a mixed population of blood cells. The method comprises the steps of: separating an amount of blood into layers that include a buffy coat layer having a mixed population of blood cells including plasma and red blood cells; providing a chamber having an opening for receiving a fluid; causing the buffy coat layer to enter the chamber; centrifuging the chamber to separate the buffy coat layer into at least a plasma containing layer, a leukocyte containing layer, and a red blood cell containing layer; and separating the leukocyte containing layer from the other layers in the chamber.

1 Claim, 11 Drawing Sheets

OTHER PUBLICATIONS

Frewin, D.B. et al. "A Comparative Study of the Effect of Three Methods of Leukocyte Removal on Plasma Histamine Levels in Stored Human Blood" in *Seminars in Hematology*, vol. 28, No. 3, Suppl. 5, Jul., 1991, pp. 18–21 1991.

Harlowe et al. "Antibodies: A Lab Manual" Cold Spring Harbor, 1988, pp. 584–589. 1988.

Högman, Claes F. et al. "The Bottom and Top System: A New Technique for Blood Component Preparation and Storage" *Vox Sang* 1988, 55, pp. 211–217. 1988.

Keller, George H. et al. "DNA Probes: Background, Applications, Procedure" MacMillan Publishers 1993, pp. 36–39; 385–403. 1993.

Lueptow, Richard M. et al. "Sedimentation of a Suspension in a Centrifugal Field" Dept. Of Mechanical Engineering, Northwestern University, Evanston, IL pp. 1–23. No Date Available.

Maniatis, T. et al. "Molecular Cloning: A Laboratory Manual" Cold Spring Harbor Laboratory, 1982, pp. 79–83. 1982.

Perrow, Jenny G. "The Preparation of Leucocyte Homogenates for Enzymatic Assays" in *New Zealand Medical Lab. Technol.*, Mar. 1977, pp. 6–9. 1977.

Rawal, Bhupat D. et al. "Evaluation of Leukocyte Removal Filters Modelled by Use of HIV–Infected Cells and DNA Amplification" in *Blood*, vol. 76, Nov. 15, 1990, pp. 2159–2161. 1990.

Sutton, Don W. et al. "Cell Separation in the Buffy Coat" om *Biorheology*, 25, 1988, pp. 663–673. 1988.

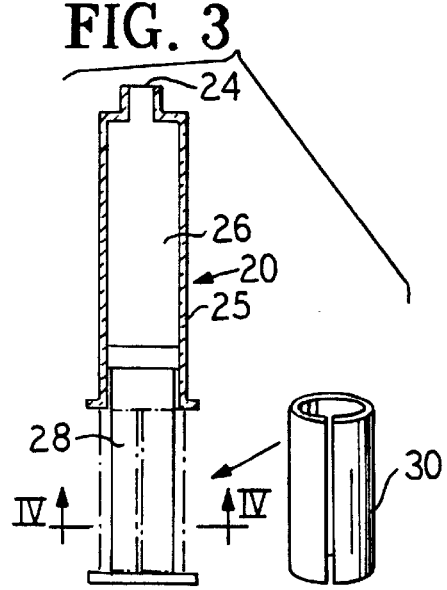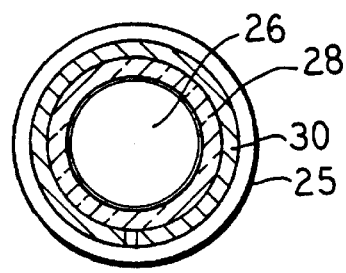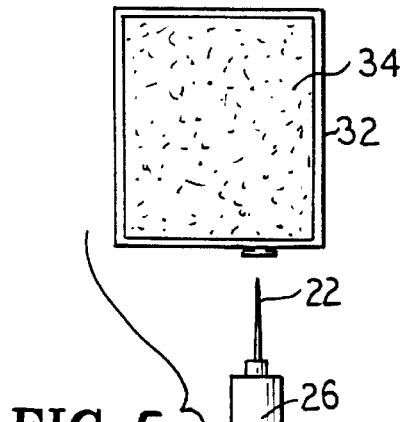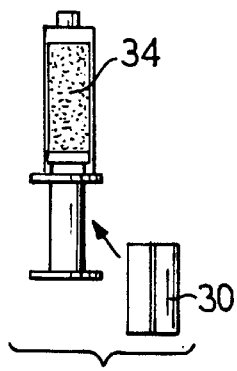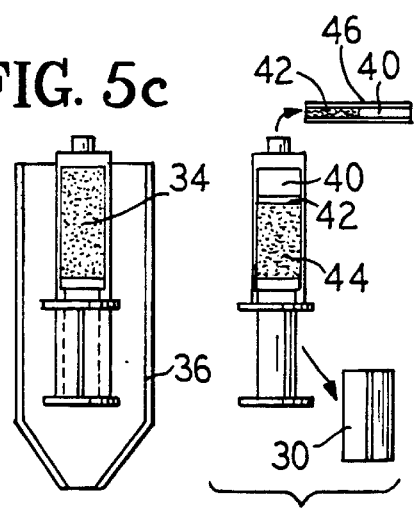

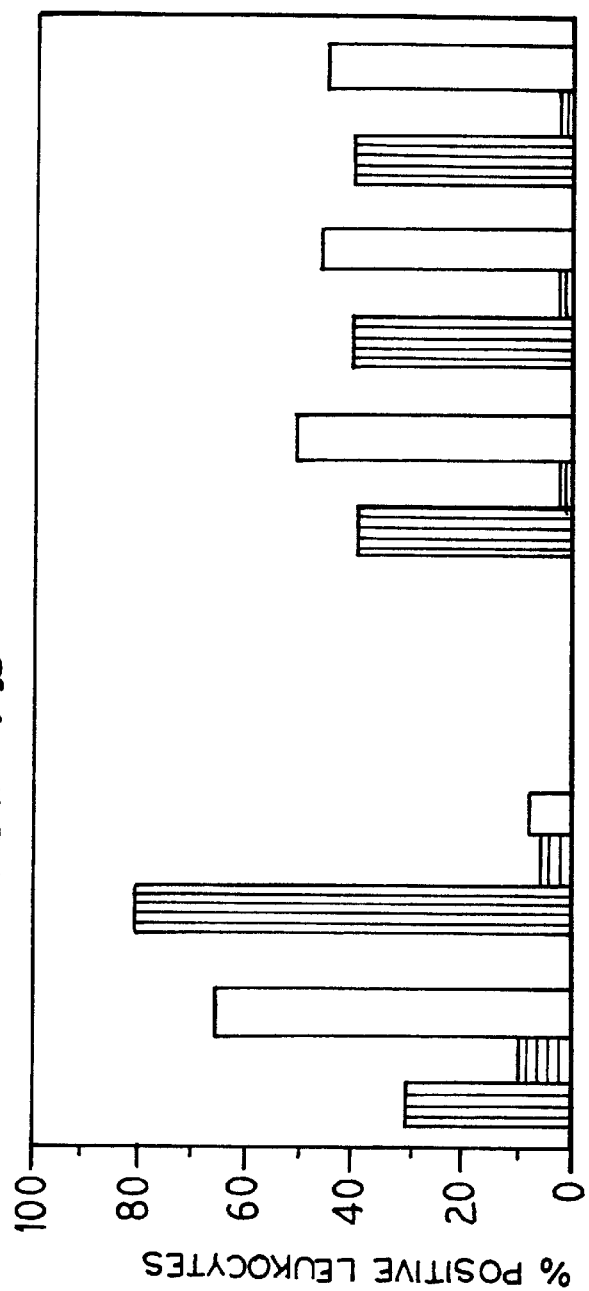

METHOD AND DEVICE FOR TESTING BLOOD UNITS FOR VIRAL CONTAMINATION

This application is a continuation of application Ser. No. 08/434,694 filed May 4, 1995, now abandoned, which is a division of application Ser. No. 08/164,517 filed Dec. 9, 1993, now U.S. Pat. No. 5,686,238, which is a continuation-in-part of application Ser. No. 08/037,525 filed Mar. 23, 1993, now U.S. Pat. No. 5,498,520, which is a continuation of application Ser. No. 07/833,285 filed Feb. 10, 1992, now abandoned.

The present invention relates generally to diagnostic techniques. More specifically, the present invention relates to the testing of blood units for viral contamination.

In a variety of therapies, such as transfusion and transplants, body fluids, especially blood components, such as red blood cells, platelets, plasma, and bone marrow, are infused from one or more individuals into a patient. Although such therapies provide treatments, some of which are life saving, that cannot otherwise be provided, due to the transmission of infectious diseases there may be potential risks to such therapies.

For example, it is known that blood can carry infectious agents, such as hepatitis virus, human immunodeficiency virus (an etiological agent for AIDS), cytomegalovirus, Epstein Barr virus, and herpes virus. Although screening methods exist to identify blood that may include such viruses, current screening methods do not assure that every blood unit that contains such a virus is identified.

In this regard, one of the difficulties in testing blood components for viral contamination, such as HIV, is that many current diagnostic tests are based on an identification of antibodies. Accordingly, they will only exhibit a positive test result if the blood unit includes antibodies for the virus, e.g., anti-HIV. With respect to intracellular viral infections, an individual, however, does not generate antibodies immediately upon infection. Rather there is a "window period" that extends from the initial infection of the patient with a virus to the generation of antibodies. When an individual is in this window period, diagnostic tests that are based on antibodies will not identify the individual, or the blood unit, as being infected. But, even though antibodies are not present, the blood unit can still transmit an infection.

It is believed that this window period, with respect to HIV infection, extends from approximately six weeks to 48 months. During this time period, an individual who has been infected with HIV and accordingly, whose blood will transmit same, will register a negative antibody response. Therefore, current screening methods will not identify as viral contaminated a blood unit from an individual who is infected with HIV but who has not generated anti-HIV.

In order to identify blood units that may be contaminated because an individual is within the window period, recent attempts have focussed on the use of nucleic acid sequencing diagnostic techniques. Specifically, attempts have been made to use polymerase chain reaction (PCR) techniques for detecting nucleotide sequences for HIV virus.

A number of methods of using PCR are known. Briefly, in one PCR method, a sample containing DNA is placed in a reaction tube including appropriate buffers, nucleoside triphosphates, a thermostable DNA polymerase and oligonucleotide primers complementary to the ends of a region of DNA of interest. Initially, to denature the double-stranded DNA under study, the temperature of the reaction is rapidly increased. The temperature is then decreased allowing the oligonucleotide primers to anneal to their complementary sequences. By increasing the temperature, a DNA extension occurs at the optimal temperature of activity for the polymerase. By repeating these cycles of denaturation-annealing-extension, a single sequence of a few hundred base pairs can be amplified. This amplification can be in the range of a factor of $10^6$ and detected with relative ease. Conway, "Detection of HIV-1 by PCR in Clinical Specimens", "Techniques in HIV Research", Stockton Press (1990).

Although nucleic acid sequencing techniques are very sensitive, they are also sample specific. Moreover, the samples of the blood units so tested are rendered unusable for therapeutic applications. Because of this, currently nucleic acid sequencing diagnostic methods do not provide a method for insuring that blood units do not have viral contamination.

For example, if one were to attempt to use a PCR technique to test a sample of a blood unit using standard technology, one could not insure that the unit did not contain viral contamination even if the test was negative. In this regard, because a PCR test is sample specific unless the whole blood unit was tested, it would not accurately reflect that the unit did not include viral contamination; if only a 10 ml sample were tested, the remaining 290 ml of a 300 ml could contain a viral contaminant.

A PCR test will only determine if there is a viral agent in the sample being assayed, not in the entire unit. Because the test destroys the viability of the component, heretofore, it was not possible to test the entire component to ensure that it is not contaminated with, for example, HIV.

Accordingly, there is a need for improved diagnostic testing of blood units to determine viral contamination during the "window period" of contamination.

SUMMARY OF THE INVENTION

The present invention provides a method for testing a blood unit for viral contamination that does not render the blood unit unusable for therapeutic applications. The method allows one to effectively sample the entire blood unit using, for example, nucleic acid sequencing techniques. The method improves the accuracy of diagnostic tests for viral contaminants.

Although typically to increase the accuracy of a diagnostic test for infectious disease it is desirable to increase the sample volume of the material being assayed, with respect to blood components this is not possible. In the case of blood and its components, only a small fraction of the total volume of the blood component can be sacrificed for performance of diagnostic assays for infectious diseases. The inability to sample the whole blood unit places a finite limit on the accuracy of diagnostic testing (including nucleic acid amplification technology) due to sampling volume. In this regard: 1) the assay result can be a true negative, but the unit positive; or 2) the assay result can be a false negative due to lack of sensitivity of the assay. The present invention addresses both of these limitations.

To this end, the present invention provides a method for testing a blood unit for viral contamination without rendering the blood unit unusable for therapeutic applications. The method comprises the steps of: removing and collecting from a blood unit a majority of the leukocytes present therein; and using the collected leukocytes to test the blood unit for viral contamination.

In an embodiment, the present invention provides a method for testing a blood unit for viral contamination without rendering the blood unit unusable for therapeutic applications comprising the steps of separating the blood unit into a plasma rich platelet component, a buffy layer, and a red blood cell component; removing the buffy layer; and assaying the buffy layer for viral contamination.

In a preferred embodiment, the present invention provides a method for creating a leukocyte rich sample from a mixed population of blood cells comprising the steps of separating an amount of blood into layers that include a buffy coat layer having a mixed population of blood cells including plasma and red blood cells; providing a chamber having an opening for receiving a fluid; causing the buffy coat layer to enter the chamber; centrifuging the chamber to separate the buffy coat layer into at least a plasma layer, a leukocyte layer, and a red blood cell layer; and separating the leukocyte layer from the other layers in the chamber.

In an embodiment, the leukocyte layer includes less than or equal to $5 \times 10^8$ red blood cells.

In an embodiment, the leukocyte layer includes less than or equal to $5 \times 10^9$ platelets.

In an embodiment, the chamber is exposed to a centrifugational force of at least 300×g.

In an embodiment, the chamber is exposed to a centrifugational force of approximately 750×g.

In an embodiment, the chamber is centrifuged for approximately 5 to about 10 minutes.

In an embodiment, the chamber is defined by a syringe.

The present invention, in another embodiment, provides a method for testing a blood unit for viral contamination without rendering at least a platelet rich plasma layer and a red blood cell rich layer of the blood unit unusable for therapeutic applications comprising the steps of: separating an amount of blood into a platelet rich plasma layer, a red blood cell rich layer, and a buffy layer that includes a mixed population of blood cells including plasma and red blood cells; providing a chamber having an opening for receiving a fluid; causing the buffy coat layer to enter the chamber; centrifuging the chamber to separate the buffy coat layer into at least a plasma layer, a leukocyte layer, and a red blood cell layer; separating the leukocyte layer from the other layers in the chamber; assaying the leukocyte layer to determine viral contamination; and if the assay determines no viral contamination is present in the leukocyte layer using at least one of the platelet rich plasma layers or red blood cell rich layer for therapeutic applications.

In another embodiment, a method for testing a blood unit for viral contamination without rendering at least either a platelet rich plasma layer or a red blood cell rich layer of the blood unit unusable is provided comprising the steps of: separating an amount of blood into layers that include a buffy coat layer having a mixed population of blood cells including plasma and red blood cells; providing a syringe having an opening for receiving a fluid, a chamber, and a plunger received within the chamber; causing the buffy coat layer to enter the chamber; securing means for preventing axial movement of the plunger into the chamber around at least a portion of the plunger; centrifuging the syringe to separate the buffy coat layer into at least a plasma layer, a leukocyte layer, and a red blood cell layer; and separating the leukocyte layer from the other layers in the chamber.

Additionally, the present invention provides a system for use in obtaining a leukocyte rich sample from a mixed population of blood cells. The system includes a syringe including a chamber having a first opening for receiving a fluid and a plunger received within the chamber for causing fluid to be urged into and out of the chamber. The system also includes removable means that prevents the plunger from axial movement into the chamber. In an embodiment, the means is a sleeve coupled around at least a portion of the plunger. In an embodiment, the syringe includes a cannula extending from the opening.

Additional features and advantages of the present invention are described in, and will be apparent from, the detailed description of the presently preferred embodiments and from the drawings.

BRIEF DESCRIPTION OF THE DRAWINGS

FIG. 3 illustrates an embodiment of the modified syringe of the present invention.

FIG. 4 illustrates a cross-sectional top view of the embodiment of the syringe of FIG. 3 taken along lines IV—IV.

FIGS. 5a–5d illustrate, schematically, an embodiment of the process of the present invention.

FIG. 9b illustrates graphically test results from Example No. 1 and specifically, phenotype of cells pre and post processing of buffy coat preparations at different centrifugation speeds with an embodiment of the syringe of the present invention for a 48 hour old buffy coat.

DETAILED DESCRIPTION OF THE PRESENTLY PREFERRED EMBODIMENTS

Figure 1:
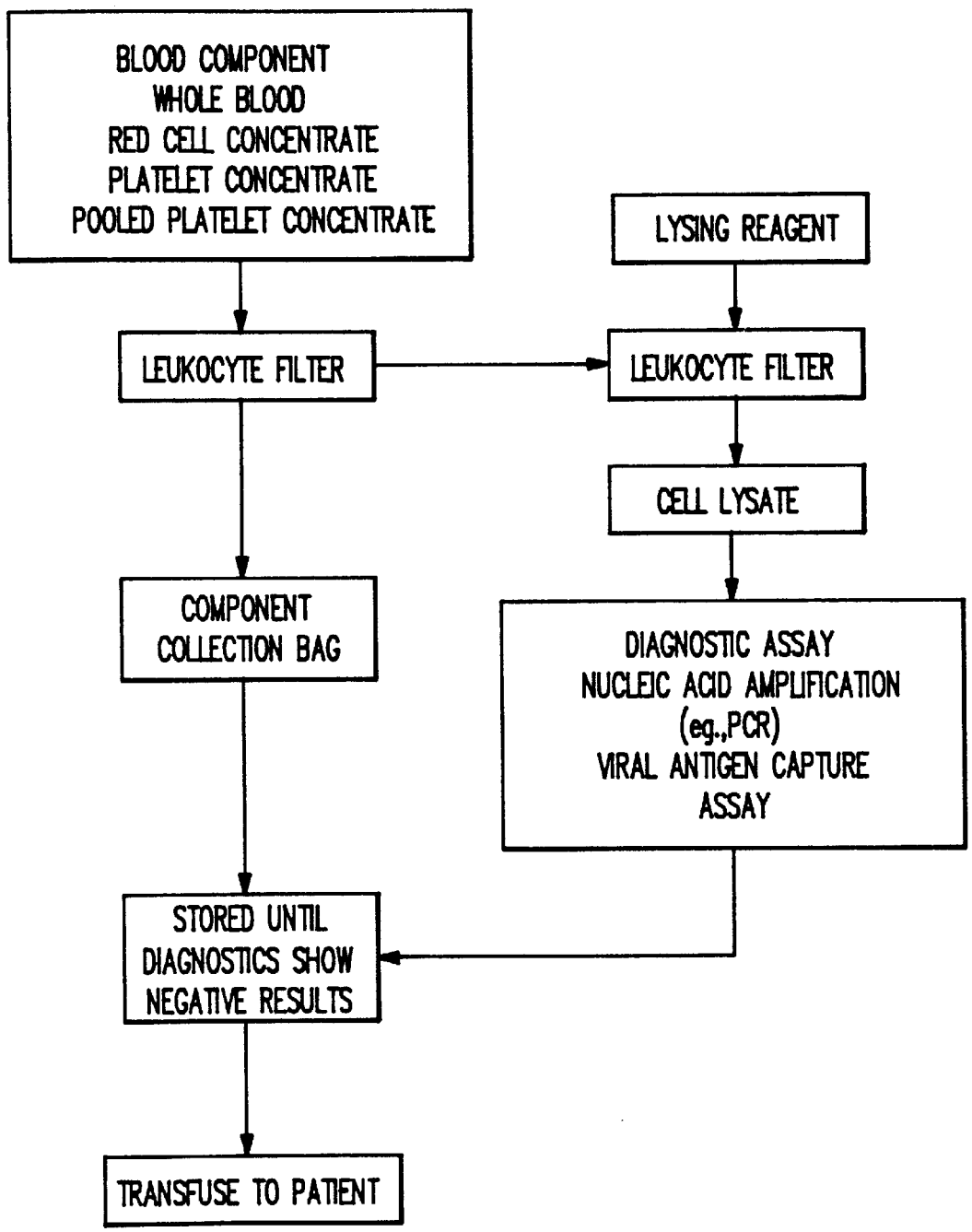
FIG. 1 illustrates schematically an embodiment of the method of the present invention for testing a blood component for viral contamination.

The present invention provides an improved method for testing a blood component for a viral contaminant. The method of the present invention improves the accuracy of diagnostic tests without sacrificing the blood unit to be administered. Additionally, the present invention provides an apparatus and improved system for testing blood compounds. To this end, the present invention allows the entire unit of whole blood, red blood cells, or platelet concentrate to be sampled for viral contamination without rendering the cell product unusable for therapeutic applications.

In an embodiment, the invention includes the steps of using a modified syringe to collect a buffy coat fraction from a whole blood separation process that separates blood into layers including a buffy coat layer that has a mixed population of leukocytes, red blood cells, and platelets. After the syringe has received the buffy coat layer, means for preventing the plunger from moving into the syringe chamber are attached to the syringe. The syringe is centrifuged. Due to the means for preventing, the plunger does not move into the syringe chamber, preventing the buffy coat layer from being expelled from the syringe.

The buffy coat through the centrifuge process is separated into plasma, leukocytes (white blood cells) and red blood cells. The plasma can then be expressed off the leukocytes and the leukocytes can be easily segregated for testing. Thus, a rich leukocyte sample is captured without damaging the blood components. The methods and devices for so capturing the leukocytes will be set forth in detail hereinafter.

There are three principal indications for the transfusion of a blood product: 1) deficiency in oxygen-carrying red blood cells; 2) deficiency in hematologic factors related to blood clotting, includes platelets or protein coagulation factors; and 3) deficiency in plasma volume. Patients requiring a transfusion do not receive whole blood but the specific component required to overcome the clinical deficiency. For example, patients undergoing chemotherapy or radiation therapy require primarily platelets and to a lesser degree red cells. Bone marrow or other organ transplant and dialysis patients generally require only red blood cells.

Leukocytes are unwanted because they are not relevant to the therapeutic effects of oxygen-carrying red blood cells, platelet or plasma, and have been implicated as increasing the risks associated with blood transfusion for their role in alloimmunization to HLA antigens and post transfusion infection by acting as virus carrying cells. Typically, the leukocytes are removed by a filtering process in approximately 10% of the blood components that are transfused.

When a filtering process is used, the leukocytes captured in these filters are discarded. As set forth in detail below, in an embodiment of the invention, the filters containing the leukocytes can be used as a starting material for a process to recover and/or amplify viral markers (viral nucleic acid sequences and/or antigens).

Pursuant to an embodiment of the present invention, a majority, greater than 50%, of the leukocytes are collected. Depending on the method used, up to 99.8% of the leukocytes may be collected. Leukocytes typically comprise 0.25% of the cellular composition of blood. A leukocyte count of 7.5 million/ml of blood is considered average for an adult. In a 500 ml unit of whole blood, containing 63 ml of anticoagulant solution, $3.2 \times 10^9$ leukocyte cells will be present.

Because the leukocytes are a source of infectivity in the blood, they provide a desirable material for diagnostic assays. Furthermore, because the collected leukocytes are derived from the entire unit of blood component to be transfused, as opposed to a small segment thereof, an improved diagnostic procedure is achieved.

FIG. 1 illustrates schematically an embodiment of the process of the present invention. The blood component (which can be whole blood, red cell concentrate, platelet concentrate, or pooled platelet concentrate) is first passed through a filter which is designed to capture 90 to greater than 99% of the leukocytes present.

Leukocyte filters that can be used pursuant to the present invention include the Sepacell R-500 filter available from Asahi Corp., Tokyo, Japan and the RC-100 for blood filtration and PL-100 for platelet filtration, both available from Pall Biomedical Corp., East Hills, N.Y. It has been reported in Biotechnology & Medical, Aug. 19, 1988 that an Asahi filter is able to remove 99.8% of the leukocytes present in whole blood.

The filtered blood component is collected in a blood collection bag. The blood component is stored pending the results of the diagnostic test.

Pursuant to an embodiment of the present invention, the leukocyte filter is utilized as a source material for diagnostic tests for infectious disease antigen and nucleic acid sequences. To this end, the filter is treated to lyse the cells contained in the filter. This allows the recovery of nucleic acids and antigens that are contained on and within the leukocytes.

The cells are lyse by using a lysing reagent. The lysing reagent preferably will be a solution containing a detergent to break the cytoplasmic membrane and release the nuclei of the cells.

The cell lysate is then flushed out of the filter using an isotonic saline solution and collected. This resultant cell lysate is then used as a test material for diagnostic assays (nucleic acid amplification technology for viral nucleic acid sequences, e.g., PCR or 3SR or viral antigens, e.g., enzyme-linked immunoadsorbent assays).

Because the assay, pursuant to the present invention, will be based on an analysis of the great majority of the leukocytes present in the blood unit, even when using sample specific analysis such as PCR methods one can be assured that a negative result is accurate even if an individual is in a window period of infection.

Once a negative result is obtained using the cell lysate, the blood component contained in the collection container can then be transfused into a patient.

Figure 2:
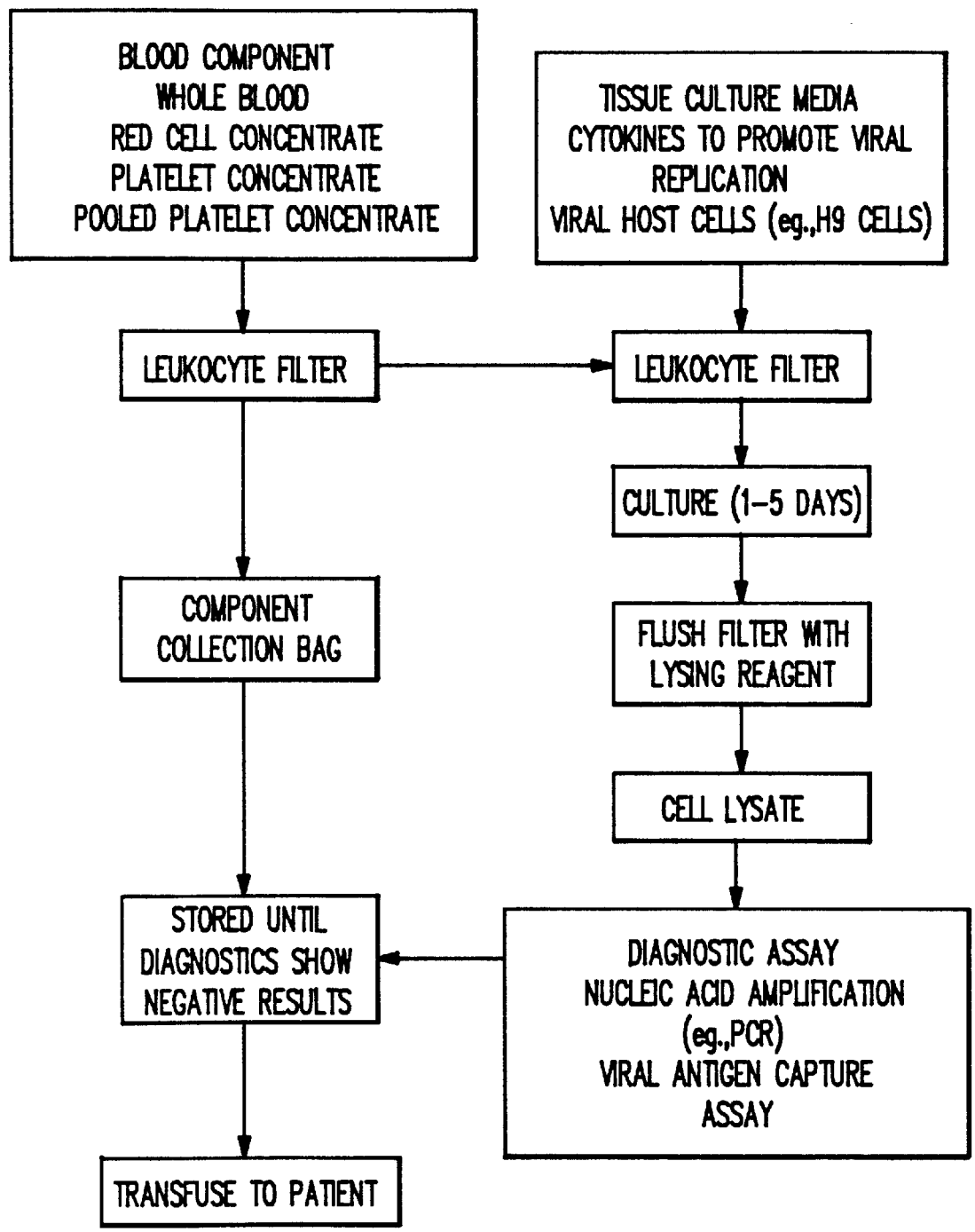
FIG. 2 illustrates schematically a further embodiment of the method of the present invention for testing a blood component for viral contamination.

FIG. 2 illustrates schematically another embodiment of the present invention. If necessary to increase assay sensitivity (particularly for antigen capture assay systems), the leukocyte filter can be utilized as a culture chamber for viral replication.

In this case, again a blood component (whole blood, red cell concentrate, platelet concentrate, or pooled platelet concentrate) is filtered through a leukofilter. The leukofilter is separated from the blood bag container, containing the filtered blood component, and the filter is flushed with tissue culture media such as 10% Fetal Calf Serum in RPMI 1640 media. In some cases, it may be desirable to supplement the media with cytokines (e.g., IL-2 or T-cell mitogen (e.g., PHA)) to promote viral replication in the leukocytes and to sustain the viability of the cells in the filter.

In addition, in some cases, it may be desirable if the tissue culture media is supplemented with viral host cell lines (example H9 cells for HIV). In this case, the filter would be used as a culture chamber for the leukocytes captured from the blood and for virus host cells. The H9 cells can then be infected by HIV present in the captured leukocytes and can serve to amplify the production of viral antigen (e.g., HIV p24 antigen).

After the appropriate culture period of approximately 1 to 5 days, the filter can be treated to accomplish lysis of the trapped cells by one of several means (freeze-thaw, detergent, hypotonic shock). The resulting cell lysate can then be collected by flushing the filter with an isotonic saline solution.

The collected cell lysate can be tested using conventional antigen capture assay systems such as, for example, DuPont HIV p24 Care Profile, Elisa Kit or Coulter HIV p24 Antigen Assay (Hialeah, Fla.) for the HIV p24 antigen or by nucleic acid amplification methodologies, such as Gene Amplimer HIV-1 Reagents with GeneAmp® PCR Core Reagents and Perkin-Elmer Cetus DNA Thermal Cycler, available from Perkin-Elmer Cetus. In some cases, the cell lysis may not be required due to release of the virus into the tissue culture media from infected cells.

Again, by using this method, even if a sample specific diagnostic test is used, because the test is with respect to the great majority of leukocytes present, a negative test will ensure that the blood component is not contaminated. The blood component contained in the blood bag container can then be transfused into a patient.

In an embodiment of the method of the present invention, instead of filtering the blood component to capture the leukocytes, a centrifugation process that separates a whole blood unit into various components can be used. During a typical centrifugation process, the whole blood is separated into a top portion including platelet rich plasma, a middle or buffy coat layer containing white cells and leukocytes, and a bottom red blood cell rich layer. Typically, the buffy coat layer is discarded.

Pursuant to the present invention, the buffy coat layer is used for diagnostic applications. To this end, the buffy coat can be subjected to nucleic acid amplification, e.g., PCR or 3SR or viral antigen capture assay. By testing the buffy coat layer, if a negative test results, one is assured that both the platelet rich plasma component and red blood cell component are viral contaminant free. It is believed that by collecting the buffy coat using standard techniques, at least approximately 80% of the leukocytes are recovered.

In an embodiment, the following method is used:
1. Centrifuge the blood bag in an inverted position in a refrigerated centrifuge containing whole blood at 5° C. using a "heavy" spin.
2. Hang the centrifuged, inverted bag on a ring stand or inverted plasma expresser. The temperature of the blood must not exceed 10° C. during the procedure. Allow the bag to hang undisturbed for several minutes.
3. Place the transfer bag on a scale (e.g., dietary scale) below the blood bag. Adjust the scale to zero.
4. Penetrate the closure of the primary bag, avoiding agitation of the contents and allow red blood cells to flow to the transfer bag. At least 80% of the red blood cells must be transferred to the satellite bag. To calculate the amount of red blood cells to be expressed estimate the amount of blood (excluding anticoagulant) in the bag multiplied by the donor's hematocrit (assume 40% for females and 43% for males) (1 ml of red blood cells (RBC) weighs 1.06 gm).
5. The remaining blood in the bag contains the buffy coat, some residual red blood cells, and the plasma.
6. The contents are mixed and the preparation is centrifuged to pellet the buffy coat.
7. The plasma is expressed into a satellite container.
8. The residual red cells in the buffy coat can be lysed by adding a hypotonic ammonium chloride solution or other red cell lysing reagent to generate a purified buffy coat preparation.
9. This cell preparation would be processed for PCR or other analysis using standard methodologies. In an embodiment, preferably, the buffy coat is collected within 24 hours from the time of donation.

Other methods can be used to obtain the buffy coat, using a device available from subsidiaries of Baxter International sold under the trademark Optipress® and using disposables sold under the trademark Optipak®. Reference is also made to U.S. Pat. Nos. 4,350,585 and 4,608,178, the disclosures of which are hereby incorporated herein by reference.

Using traditional separation methods, the resultant buffy coat layer that is obtained has a mixed population. The layer thereby includes in addition to leukocytes, platelets, and red blood cells. This additional population may interfere with a PCR analysis of the leukocytes that are present in the buffy coat. Pursuant to the present invention, a method is provided for creating a substantially purified leukocyte sample from a traditionally obtained buffy coat layer that has a mixed population.

To this end, after a fraction of the buffy coat is collected through typical methods using, for example, an Optipress® device, a modified syringe can be used to collect the buffy coat fraction. Referring now to FIG. 3, in an embodiment, the syringe 20 includes a body 25, an opening 24 and a chamber 26. Preferably, as illustrated in FIG. 5, the syringe includes a cannula 22. However, it is not necessary, in certain applications, to provide a cannula on the syringe. Additionally, depending on the application or use, the cannula may be a pointed cannula or a blunt cannula.

Received within the chamber 26 is a plunger 28. The plunger 28 causes fluid to be sucked into the chamber 26 and expelled therefrom as is known in the art.

Additionally, the modified syringe system 20 includes a plunger sleeve 30. The plunger sleeve 30 prevents, as discussed in detail below, the plunger from moving into the chamber 26.

FIGS. 5a–5d illustrates schematically an embodiment of the method of the present invention. In use, the cannula 22 pierces a container 32 including a buffy coat fraction 34 that includes a mixed population. The container can contain blood that has been separated into layers including a buffy coat layer, or the container 32 as illustrated can only contain the buffy coat layer 34. The amount of buffy coat collected can vary depending on the component that was separated and the volume of same. Therefore, the volume of the chamber can, if desired, likewise vary.

Once the cannula 22 has pierced the container 32, the buffy coat layer is collected by pulling the plunger 28 out of the chamber 26. This causes the buffy coat layer 34 to be received by the chamber 26 of the syringe 20.

Pursuant to the present invention, after the buffy coat 34 has been received within the syringe 20, and specifically, the chamber 26, the plunger sleeve 30 is located over the plunger 28. Although, in the illustrated embodiment, the plunger sleeve is a piece of plastic that includes a slit 31 so it that can be slipped over and coupled around the plunger 28, any means for preventing movement of the plunger can be utilized. For example, the plunger sleeve 20 could comprise a member having a hinge allowing the sleeve to be opened and coupled around the plunger. Likewise, the plunger sleeve could be a multi-piece member that is secured around the plunger. The plunger sleeve 30 prevents axial movement of the plunger 28 into the chamber 26 of the syringe 20.

After the plunger sleeve 30 has been secured to the syringe 20, the syringe 20 can then be centrifuged. To this end, preferably, the cannula 22 is removed and the opening 24 is removably sealed with a cap or other means. As illustrated in FIG. 5c, the syringe 22 is then placed within a centrifuged tube 36. By way of example, if a 5 cc syringe is used, a 50 cc centrifuge tube can be used to receive the syringe.

The syringe 22 is then centrifuged causing the buffy coat mixed population to separate into a plasma layer 40, a leukocyte layer 42, and a plasma rich red blood cell layer 44. This separation is due to the different densities of the cellular components in the buffy coat 34. As illustrated in FIG. 5d, the heaviest of the cells, the erythrocytes become packed at the bottom of the chamber 26 with leukocytes and platelets forming sequential layers within the chamber 26 of the syringe 20. As illustrated in FIG. 5d, therefore, the plasma layer 40 will be the first layer, the leukocyte layer the second layer, and the red blood cell layer 44 the third or bottom layer.

After the centrifugation process, the leukocyte layer 42 is separated from the remaining layers for PCR analysis. A variety of methods can be used to so separate the layers. In the illustrated embodiment, a sample collection tubing 46 can be coupled around the opening 24 of the syringe 20. The plunger sleeve 30 is removed, and the plunger 28 is then biased into the chamber causing first the plasma layer 40 to be expressed through the sample collection tube 46. This layer should be substantially clear or have a slightly yellow color.

The leukocyte layer 42 will then be expressed into the sample tube 46 after the plasma layer 40. The practitioner can easily determine when the leukocyte layer 42 is beginning to be received in the collection tube 46 as it has a white color distinct from that of the plasma. Once the entire leukocyte layer 42 has been received within the sample tube 46, the tube is then sealed. The practitioner can easily determine the line of demarcation between the leukocyte layer 42 (white in color) and the red blood cell layer 48 (red in color). The tube 46 can be sealed through a variety of means including heat sealing.

The tube 46 containing the leukocytes then can be used for PCR analysis. If desired, for example, the leukocytes can be transferred to another container for PCR diagnostics or storage.

As an alternative to using a tube to collect the leukocytes, a vacutainer tube (not illustrated) can be used. To this end, a smaller syringe sleeve (not illustrated) would be attached to the chamber plunger that would stop when a given volume of sample is collected while using the vacutainer tube to draw out the sample.

The method of the present invention allows the collection of a high concentration of leukocytes in less than 15 minutes with minimum technique manipulation. Additionally, the syringe 20 and chamber 26 is a closed system that will decrease exposure of the blood center technicians to blood borne pathogens. The collected leukocytes from the chamber 26 will be a substantially pure, rich collection of leukocytes that can be used as a source of cells for screening the blood products for viral contaminants including HIV, CMV, and hepatitis.

Additionally, an advantage of the method of the present invention is that it provides a sample of leukocytes that has a low level of red blood cell contamination that allows the sample to be used directly in PCR analysis. Further, by using tubes to store the leukocytes, the tubes can be labeled with, for example, bar codes that will decrease the possibility of mislabeling samples.

By way of example, and not limitation, an example of the present invention will now be set forth.

EXAMPLE NO. 1

This experiment validates the methodology that isolates leukocytes using the device and method illustrated in FIGS. 3–5 from a buffy coat preparation obtained using an Optipress® apparatus and Optipak® disposables, hereinafter, for the sake of brevity, referred to as the Optipress® device. The studies focussed on the collection of a leukocyte rich sample from a mixed population of blood cells (erythrocytes, platelets, leukocytes) using the syringe chamber of FIG. 3 at different centrifugation forces and times.

Cell Sources

Buffy coats were prepared from whole blood units of various ages purchased from Interstate Blood Bank or from in-house donors using the Optipress® device. Briefly, the whole blood units were centrifuged at >3500×g (High Speed) or processed using the Optipress system. The high speed buffy coat preparation (35–50 mls) contains leukocytes and high concentrations of platelets and red blood cells (mean HCT=⁻55%). The slow speed buffy coat preparations contain leukocytes with lower levels of contaminating platelets and red blood cells (mean HCT=42.4%). The buffy coats were held at room temperature until used in the separation protocols.

Monoclonal Antibodies

Mouse IgG monoclonal antibodies conjugated with fluorescein (FITC) or phycoerythrin (PE) were purchased from Becton Dickinson, Mountain View, Calif. The monoclonal antibodies with specificity to: CD3 (Leu 4), CD4 (Leu 3), CD8 (Leu 2a), CD14 (Leu M3), CD16 (Leu 11c), CD11b (anti-Cr3), CD19 (Leu12) or CD45 (HLe) were used to measure the distribution of the different leukocyte subpopulations before and after separation in the syringe chamber.

FACS Lysing Solution

FACS lysing solution was purchased from Becton Dickinson, Mountain View, Calif. as a 10× concentrate and diluted to a working 1× solution with Sterile Water prior to use. The lysing reagent is used to lyse red blood cells following direct immunofluorescence staining of whole blood or blood products (blood products with high levels of RBC contamination) with monoclonal antibodies prior to flow cytometric analysis.

Modified Syringe Leukocyte Collection Chamber

The modified syringe leukocyte collection chamber uses a 5 ml disposable plastic syringe illustrated in FIG. 3. Other components of the device are a detachable syringe sleeve, tubing, and a sample collection tube. Leukocyte separation within the chamber is based on the different densities of the cellular components within blood.

Cell Separation Methods

Different centrifugation forces and times were evaluated when performing the leukocyte separations using either high or slow speed buffy coat preparations.

The chamber was loaded by drawing a 4 ml sample of the buffy coat fraction obtained using the Optipress® device into the chamber. The syringe sleeve was then attached to the plunger to prevent its collapse during centrifugation, and the chamber was placed into a 50 ml centrifuge tube. Slow speed buffy coat preparations were centrifuged for 5, 7, and/or 10 minutes at speeds ranging between 500–1000×g. High speed buffy coat preparations were separated within the syringe chambers at centrifugation speeds between 500–1500×g for 5, 7, and/or 10 minutes.

Following centrifugation, a piece of tubing was attached to the sample collection port and the plasma, platelets and buffy coat layer were expressed into a sample collection tube. A hemostat was clamped onto the tubing when the packed RBC layer were observed entering the tubing. The sample tubing was then removed from the chamber and allowed to drain into a sample tube. The leukocyte enriched samples were held at room temperature until counted and stained for FACS analysis.

Phenotypic Analysis of Cells

Cells from the pre and post modified syringe leukocyte collection chamber samples were transferred into appropriately labeled 12×75 mm polypropylene tubes and stained with the following monoclonal antibody combinations: HLeFITC, CD3PE/HLeFITC, CD4PE/HLeFITC, CD8PE/HLeFITC, CD14PE/HLeFITC, CD16PE/HLeFITC, Cr3PE/HLeFITC and CD19PE/HLeFITC. The cells were incubated for 15–20 minutes at room temperature following the addition of the monoclonal antibody.

After the staining period, the cells were resuspended in 1–2 mls of 1× FACS lysing solution and incubated 10 minutes at room temperature. Cells were collected by centrifugation 2 minutes high speed using a Serofuge centrifuge. The supernates were poured off and the cells washed 2× with PAB. After the last wash, the cells were resuspended in PAB and held on ice or refrigerated overnight until analyzed on the FACSCAN flow cytometer.

Results

The results are divided into two sections. Section I summarizes the leukocyte isolation from slow speed buffy coat preparations and Section II summarizes the leukocyte isolation from high speed buffy coat preparations.

I. Leukocyte Isolation Using Modified Syringe Leukocyte Collection Chamber of FIG. 3

A. Isolation of leukocytes from slow speed buffy coat preparations prepared from 24 hour old blood received from Interstate Blood Bank, using the modified syringe leukocyte collection chamber of the present invention.

A total of eight slow speed buffy coat preparations obtained using the Optipress® device were processed using the syringe chamber of FIG. 3. Table 1 summarizes the WBC, RBC, and platelet cell counts pre and post processing of the buffy coats within the chamber at different centrifugation forces and times.

The mean WBC concentration of the raw buffy coat samples was $3.99 \times 10^7$ WBC/ml. Processing the buffy coats at 1000×g for 5 minutes gave the highest mean number of WBC/ml recovered ($5.54 \times 10^6$). Centrifugation for 7 minutes at 1000×g gave the poorest WBC yield (Mean=$1.8 \times 10^6$), while the 10 minute sample gave an intermediate amount of WBC's (Mean=$3.4 \times 10^6$). The red blood cell (RBC) concentration decreased significantly with the increasing centrifugation times. A decrease in the RBC concentration of 1.8 logs was observed in the 5 minute, 2.2 logs in the 7 minute and 5.2 logs in the 10 minute 1000×g post chamber samples as compared to the pre chamber sample. The platelet concentrations in the post chamber samples were slightly greater than the pre chamber value.

Decreasing the centrifugation force to 750×g resulted in mean WBC/ml concentrations of $1.225 \times 10^6$, $1.7 \times 10^6$, and $3.825 \times 10^6$ using 5, 7, and 10 minute centrifugation respectively. The RBC contamination in the post chamber samples collected at 750×g decreased with increasing centrifugation times (5 minutes=1.86 logs; 7 minutes=2.45 logs; 10 minutes=5.27 logs). Platelet concentrations in the 750×g post chamber collected samples were slightly higher than the pre chamber control sample.

Processing the buffy coat preparations at 500×g for 5 minutes did not always result in the formation of a distinct WBC layer within the chamber. Therefore, a 5 minute centrifugation time at 500×g is not recommended for collecting leukocytes with the syringe chamber for PCR analysis. Centrifugation at 500×g for 7 and 10 minutes resulted in mean WBC/ml concentrations of $3.42 \times 10^6$ and $1.64 \times 10^6$ respectively. Increasing the centrifugation time from 7 to 10 minutes resulted in a significant decrease in the RBC contamination in the post chamber samples at 500×g. RBC contamination in the 10 minute sample was reduced 5.09 logs while the 7 minute sample had a 1.83 low reduction in RBC concentration as compared to the pre chamber sample. The platelet concentrations were slightly elevated in both the 7 and 10 minute 500×g post syringe chamber samples as compared to the pre chamber value.

Table 2 summarizes the phenotypes of the cells pre and post processing of the buffy coats using the syringe chamber. To analyze the major cell populations (lymphocytes, monocytes and granulocytes) an electronic gate was set to include the HLe (pan leukocyte) positive cells and exclude the HLe negative cells from the analysis. After the HLe gate was set, electronic regions were set around the lymphocyte, monocyte and granulocyte populations based on their light scattering properties (FSC vs SSC).

Figure 6:
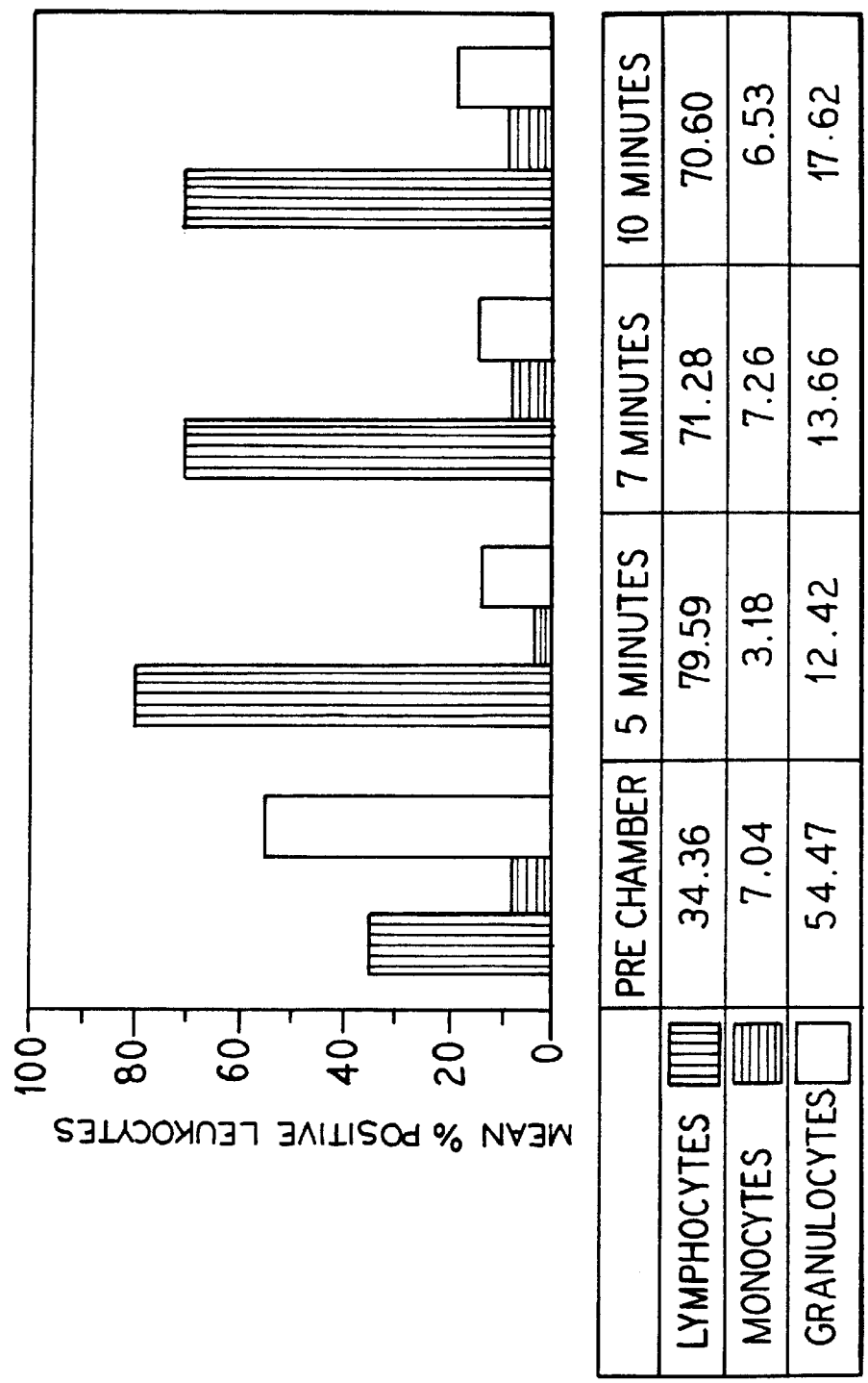
FIG. 6 illustrates graphically test results from Example No. 1 and specifically, phenotype of cells pre and post processing of slow speed buffy coat preparations at 1000×g with an embodiment of the syringe of the present invention.

The lymphocyte population in the pre chamber buffy coat samples ranged from 9.18%–61.93% with a mean value of 34.36%±16.62%. The monocyte population had a mean value of 7.04%±7.42% (range=0.19%–22.07%) while the granulocyte population had a mean value of 54.47%±19.05% (range=0.85%–76.28%). Samples collected from processing of the buffy coats with the syringe chamber at 1000×g (see FIG. 6) resulted in an increase in the lymphocyte population and a decrease in the granulocyte population. However, increasing the time of centrifugation from 5 to 7 to 10 minutes decreased the mean lymphocyte percentage (5 minutes=79.59:7 minutes=71.28%: 10 minutes=70.60%) and increased the mean granulocyte percentage (5 minutes=12.42%:7 minutes=13.66%: 10 minutes=17.62% in the post syringe chamber samples. The monocyte percentage decreased slightly in the 5 minute sample (mean=3.18%) and remained similar to the pre chamber percentage (7.04%) at 7 (7.26%) or 10 (6.53%) minutes.

Figure 7:
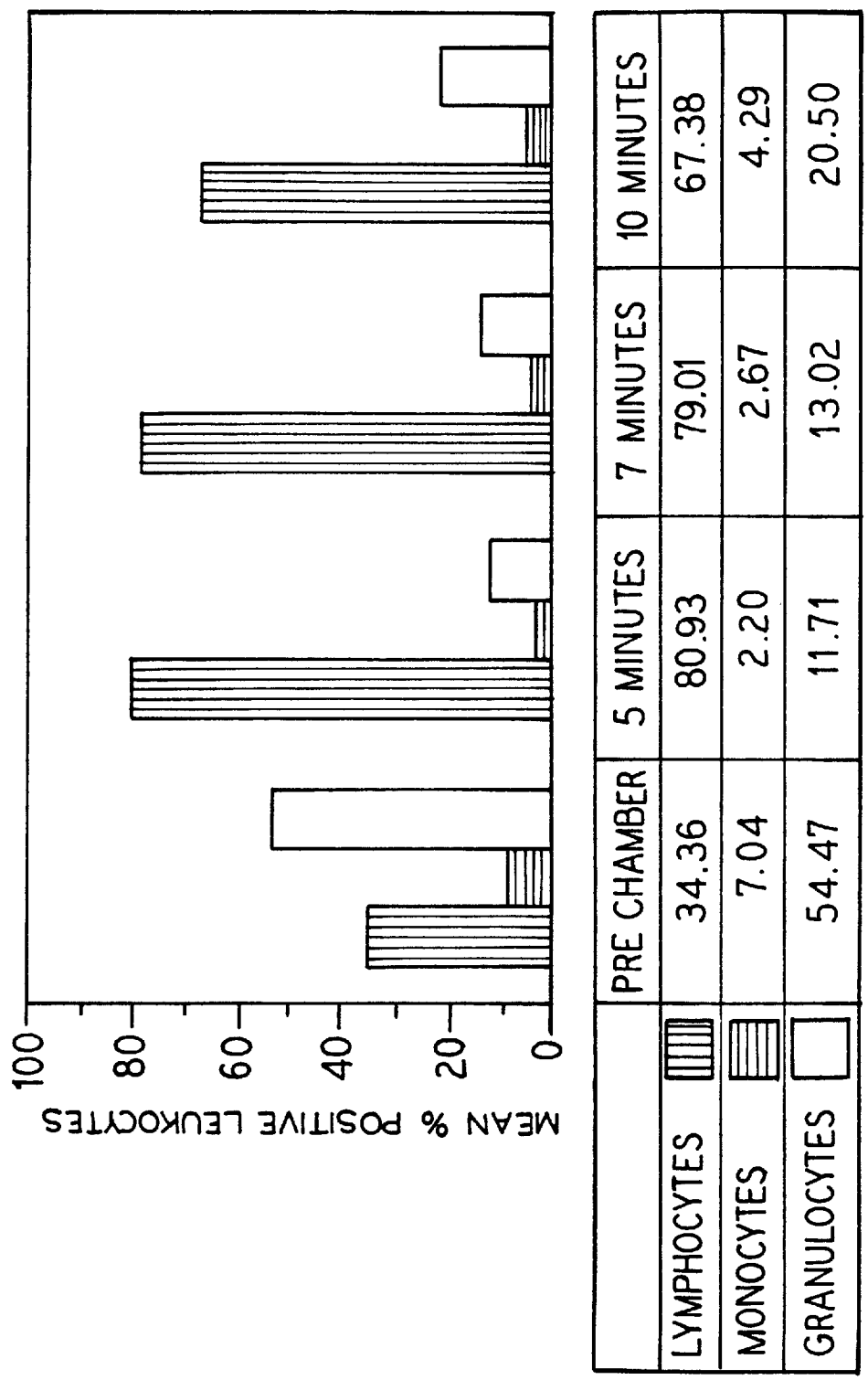
FIG. 7 illustrates graphically test results from Example No. 1 and specifically, phenotype of cells pre and post processing of slow speed buffy coat preparations at 750×g with an embodiment of the syringe of the present invention.

FIG. 7 graphically illustrates samples collected from the syringe chamber at 750×g for 5, 7, and/or 10 minutes. The lymphocyte percentage for each of the centrifugation times tested increased while the granulocyte percentage decreased as compared to the pre buffy coat control samples. Samples collected from the chambers after 5 or 7 minutes of centrifugation had similar lymphocyte (5 minutes=80.93%: 7 minutes=79.01%), monocyte (5 minutes=2.20%: 7 minutes=2.67%), and granulocyte (5 minutes=11.71%: 7 minutes=13.02%) percentages. Samples collected at 750×g for 10 minutes had lower lymphocyte (67.38%) and higher monocyte (4.29%) and granulocyte (20.50%) percentages.

Figure 8:
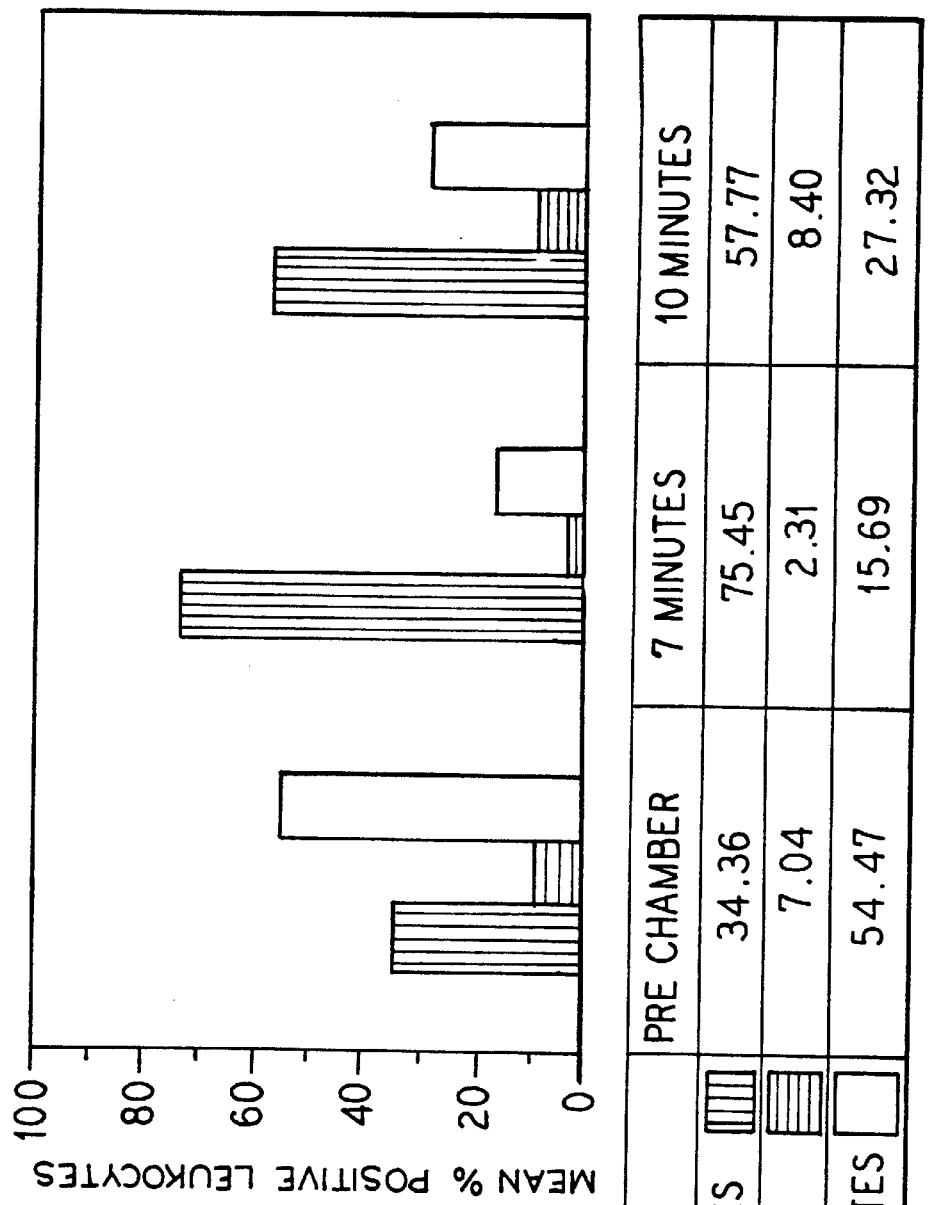
FIG. 8 illustrates graphically test results from Example No. 1 and specifically, phenotype of cells pre and post processing of slow speed buffy coat preparations at 500×g with an embodiment of the syringe of the present invention.

Post syringe chamber samples collected at 500×g for 7 or 10 minutes displayed increased lymphocyte and decreased granulocyte percentages (see FIG. 8). Samples collected from the chamber at 500×g for 7 minutes had an increased lymphocyte percentage (75.45%), and decreased percentages of monocytes (2.31%) and granulocytes (15.69%) as compared to the control buffy coat samples. Increasing the centrifugation time to 10 minutes at 500×g resulted in a lower percentage of lymphocytes (57.77%) and increased percentages of monocytes (8.40%) and granulocytes (27.32%) as compared to the 7 minute samples.

Conclusions

1) All samples collected from the modified syringe leukocyte collection chamber of FIG. 3 had increased lymphocyte percentages regardless of the centrifugation force or time as compared to the pre chamber buffy coat controls.

2) With any of the centrifugation forces tested (500, 750, 1000×g) an increase in the centrifugation time resulted in a decrease in the percentage of granulocytes in the post chamber samples. The percentage of monocytes, however, remained fairly constant regardless of the centrifugational force or time.

3) A centrifugational force of at least 500×g for 7 minutes is required to form a distinct buffy coat layer within the syringe chamber for PCR sample collection.

4) Increasing the time of centrifugation at any of the gravitational forces tested resulted in a decrease in the RBC contamination of the PCR sample collected.

5) Decreasing the centrifugational force and/or time increases the number of platelets in the PCR sample collected from the syringe chamber.

6) It appears that a centrifugation force of 750×g for 7 minutes gives the best sample for PCR diagnostics (highest lymphocyte percentage, low RBC contamination) when using the modified syringe leukocyte collection chamber of FIG. 3.

The modified syringe leukocyte collection chamber of FIG. 3 allows the collection of leukocytes from a buffy coat preparation obtained at a slow speed that is enriched for cells displaying lymphocyte light scattering characteristics. A centrifugation force of 750×g for 7 minutes appears to be the optimal conditions required to generate a sample for PCR testing. This sample for use in PCR diagnostics is enriched to a mean lymphocyte percentage of >80% and also has reduced RBC contamination.

B. Isolation of leukocytes from buffy coat preparations prepared from fresh <4 hour old blood received from in-house Fenwal donors obtained using an Optipress® device, using the modified syringe leukocyte collection chamber of FIG. 3.

Two experiments were performed to determine if the storage buffy coat fractions prior to processing with the modified syringe leukocyte collection chamber, would effect the chamber's performance. In the first experiment, a buffy coat fraction was received that had been processed using an Optipress® device from fresh in-house blood (<4 hours old). The buffy coat fraction was processed in syringe chambers at 500, 400, 300, 200, and 100×g for 10 minutes. Table 3a summarizes the cell counts pre and post processing of the buffy coat with the syringe chamber.

The white blood cell (WBC) concentration of the samples collected from the chambers increased with the decrease in the centrifugation force used to process the cells. The RBC concentration was the lowest in the 400×g sample ($7 \times 10^7$) and the highest in the 100×g ($2 \times 10^8$) sample.

Figure 9A:
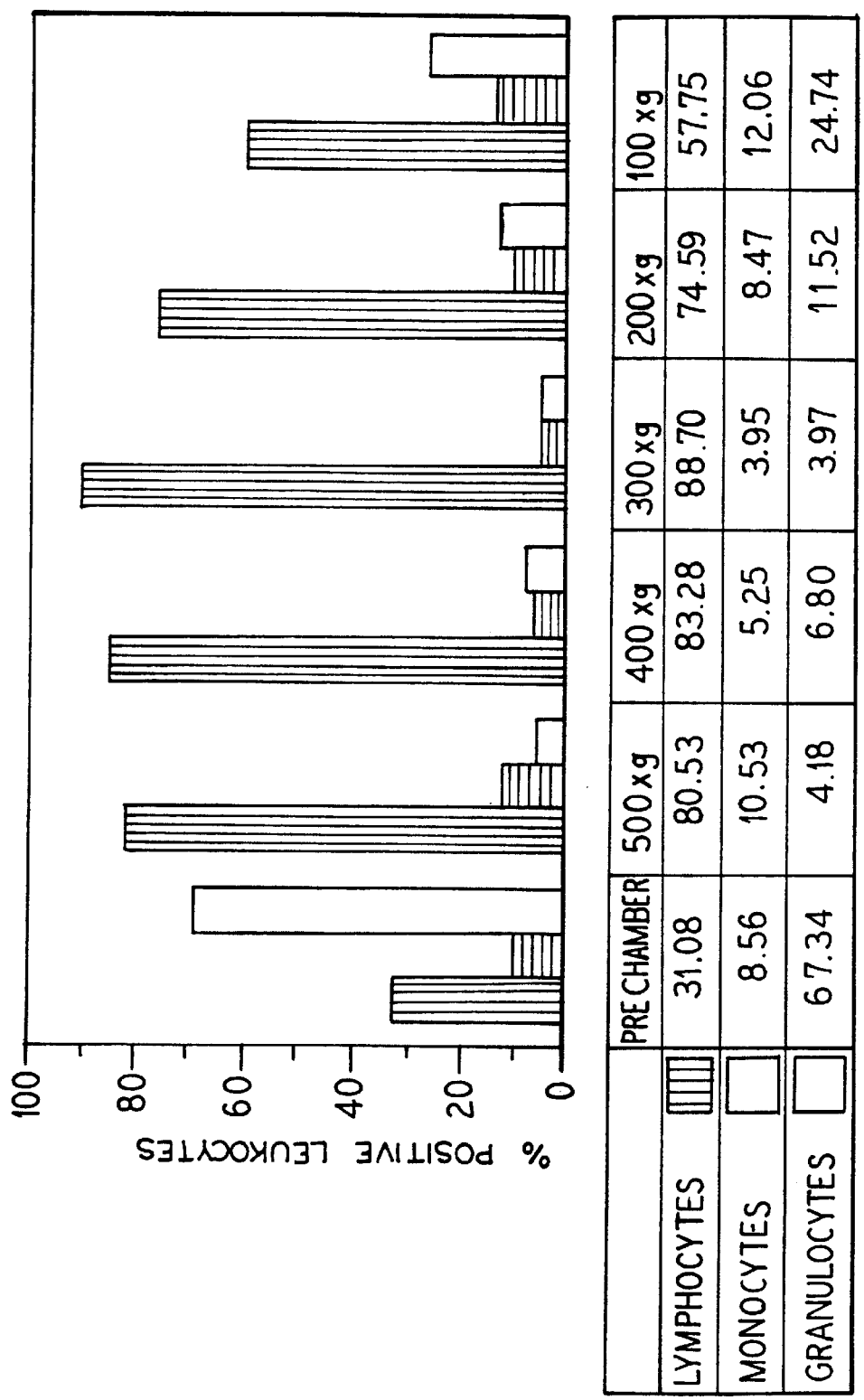
FIG. 9a illustrates graphically test results from Example No. 1 and specifically, phenotype of cells pre and post processing of buffy coat preparations at different centrifugation speeds with an embodiment of the syringe of the present invention for fresh blood, i.e., less than 4 hours old.

FIG. 9a illustrates the phenotyping results of the samples pre and post processing with the syringe chambers. The lymphocyte concentration increased from the pre chamber buffy coat control percentage of 31.08% to 80.53% at 500×g, 83.28% at 400×g, 88.70% at 300×g, 74.59% at 200×g, and 57.75% at 100×g. Corresponding to the increased lymphocyte concentration a decrease in the percentage of granulocytes in each post syringe chamber samples was observed. The monocyte concentration fluctuated from a pre chamber control value of 8.56% to post chamber concentrations of 3.95% at 300×g, 5.25% at 400×g, 8.47% at 200×g, 10.53% at 500×g, and 12.06% in the 100×g sample. The unused portion of the buffy coat was allowed to sit at room temperature for ~48 hours before being processed at 400×g for 10 minutes using a syringe chamber. WBC, RBC and Platelet concentrations in the 48 hour old buffy coat sample were comparable to the fresh buffy coat sample concentrations (Table 3a). The 48 hour old buffy coat was processed in duplicate at 400×g for 10 minutes to determine if there was any variability between the samples collected from the chamber.

Table 3b sets forth the cell counts of the samples pre and post processing with the chambers. The WBC, RBC and Platelet concentrations of the 400×g #1 and the 400×g #2 samples were similar. However, when compared to the fresh sample collected at 400×g, there was a 5 fold increase in the number of WBC/ml collected with the 48 hour old sample. The mean RBC contamination was 2.5 fold higher in the 48 hour as compared to the fresh sample. The mean platelet concentration ($5.06 \times 10^8$) was slightly lower than the platelet concentration in the freshly processed sample ($5.49 \times 10^8$).

FIG. 9b illustrates the phenotyping data of the 48 hour old buffy coat sample pre and post processing with the syringe chamber of FIG. 3. There were no apparent differences in the percentages of lymphocytes, monocytes, or granulocytes between the 48 hour old buffy coat control sample and the 400×g 10 minutes syringe chamber samples.

Comparing the freshly processed buffy coat and the 48 hour old buffy coat, the lymphocyte and monocyte percentages decreased while the granulocyte percentage increased over the storage time of the buffy coat.

In the second experiment, a buffy coat fraction was received that had been processed from fresh in-house blood (<4 hours old) using an Optipress® device. The buffy coat fraction was processed in duplicate using syringe chambers at 500, 400, 300, and 200×g for 10 minutes.

Table 4 summarizes the cell counts pre and post processing of the buffy coat with the syringe chamber. The mean, WBC concentration was the highest with the 200×g sample ($1.66 \times 10^7$) followed by the 400×g ($1.15\% \times 10^7$), 300 ×g ($9.15 \times 10^6$), and the 500×g ($5.4 \times 10^6$) post chamber samples. The RBC contamination in the post chamber samples were reduced from a pre chamber value of $4.76\% \times 10^9$ to $6.5 \times 10^7$ at 500×g, $9.0 \times 10^7$ at 400×g, $8.5 \times 10^7$ at 300 ×g and $9.0 \times 10^7$ at 200×g. Platelet concentrations were slightly higher in all of the post chamber samples as compared to the pre chamber value of $2.75 \times 10^8$ platelets/ml.

Figure 10A:
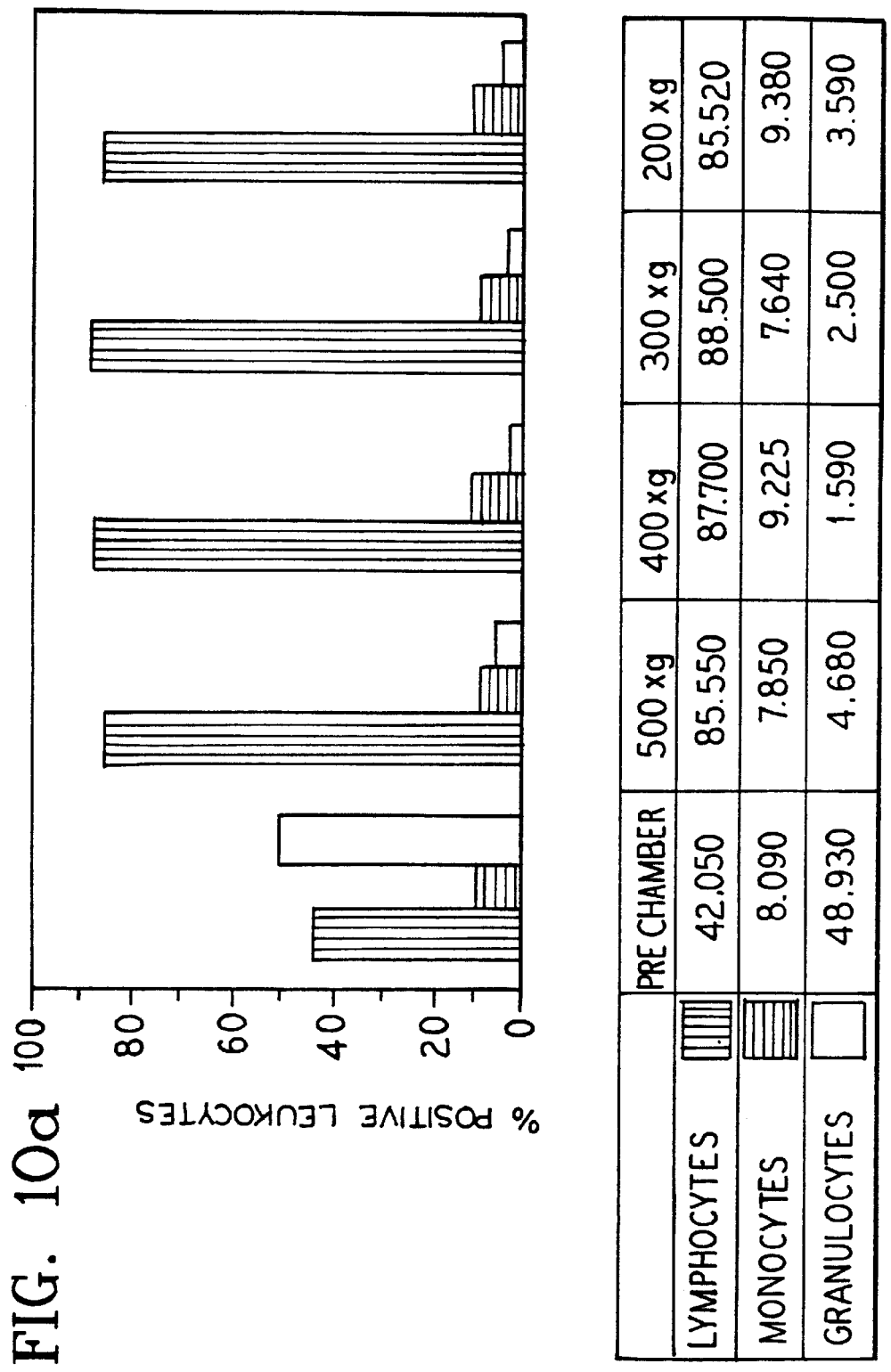
FIG. 10a illustrates graphically test results from Example No. 1 and specifically, phenotype of cells pre and post processing of buffy coat preparations at different centrifugation speeds with an embodiment of the syringe of the present invention for fresh blood, i.e., less than 4 hours old.

FIG. 10a illustrates the phenotyping results of the samples pre and post processing with the syringe chambers. The lymphocyte concentration increased from a pre chamber buffy coat control percentage of 42.05% to >82% in all post chamber samples. The monocyte concentration in all the post chamber samples were comparable to the 8.09% in the pre chamber sample. The granulocyte population decreased from a pre chamber concentration of 48.93% to <8.0% in the post chamber samples. Samples collected at the different centrifugation forces showed little variability between the duplicate samples for both the cell counts (WBC/ml, RBC/ml, Platelet/ml) and phenotype data (% Lymphocytes, % Monocytes, % Granulocytes). The buffy coat fraction was allowed to sit overnight (~24 hours) at room temperature before reprocessing with the syringe chamber at 400×g for 10 minutes. Cell counts were not performed on the 24 hour old buffy coat or the post 400×g syringe chamber sample.

Figure 10B:
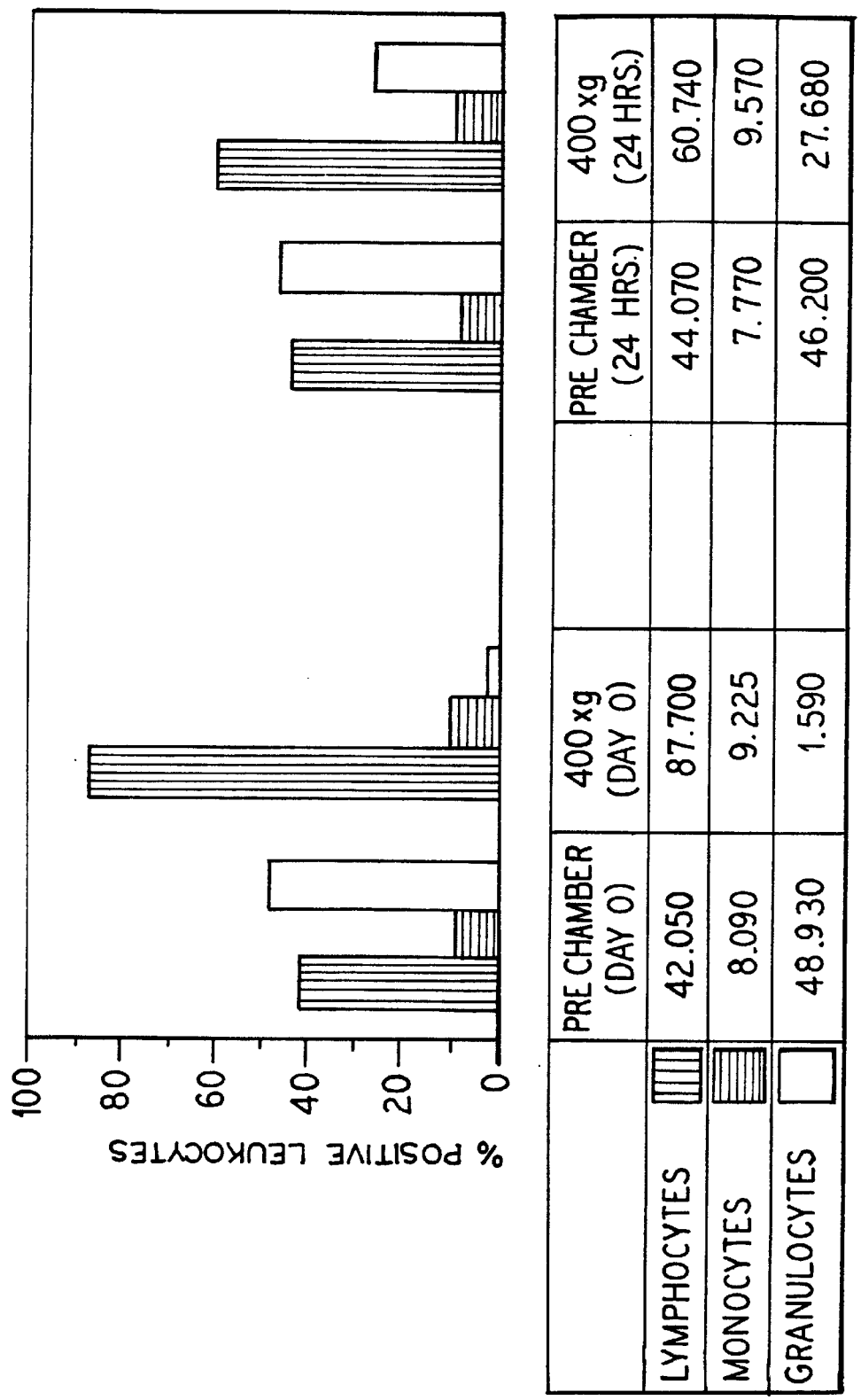
FIG. 10b illustrates graphically test results from Example No. 1 and specifically, phenotype of cells pre and post processing of buffy coat preparations at different centrifugation speeds with an embodiment of the syringe of the present invention for a 24 hour old buffy coat.

FIG. 10b illustrates the phenotype of the samples pre and post processing of the 24 hour old buffy coat with the syringe chamber. The percentage of lymphocytes increased from 44.07% in the 24 hour pre chamber buffy coat control sample to 60.74% in the 400×g syringe chamber sample. The Granulocyte percentage decreased from 46.20% to 27.68% in the post chamber sample. The monocyte concentration remained relatively unchanged between the pre chamber (7.77%) and the post chamber sample (9.57%).

Storage of the buffy coat sample, collected using the Optipress® device, for 24 hours at room temperature did not change the phenotype of the cells in the buffy coat fraction (Fresh BC: Lymphocytes=42.05%; 24 hour BC: Lymphocytes 44.07%; Fresh BC: Monocytes 8.09%; 24 hour BC: Monocytes=7.77%; Fresh BC: Granulocytes=48.93%; 24 hour BC: Granulocytes=46.20%). However, storage of the buffy coat overnight for 24 hours did have an effect on the percentages of lymphocytes harvested with the chamber at 400×g for 10 minutes. The lymphocyte percentage in the post chamber sample was decreased from a mean value of 87.7% in the fresh sample to 60.74% in the 24 hour old buffy coat. The granulocyte population increased from a mean percentage of 1.59% in the fresh sample to 27.68% in the 24 hour buffy coat post processing with the syringe chamber. The monocyte percentage in the post chamber fractions were unaffected by the storage of the buffy coat for 24 hours (Fresh=9.23%:24 hour=9.57%).

Conclusions

1) The use of "fresh" buffy coat fractions prepared from <4 hour old whole blood resulted in the collection of samples from the modified syringe leukocyte collection of FIG. 3 with >80% lymphocytes.

2) Centrifugation of the syringe chambers at 300–500×g for 10 minutes appears to yield the best samples for PCR diagnostics. Sufficient WBC numbers (>1×10$^6$), low RBC contamination, and high lymphocyte numbers (>80%) make these samples acceptable for PCR testing.

3) RBC concentration (<1×10$^8$/ml) was greatly reduced following processing of the "fresh" buffy coats in the syringe chambers.

4) Platelet concentrations are slightly higher in the post syringe chamber samples as compared to the unprocessed pre chamber buffy coat sample. Platelet concentrations collected within the chamber should not affect the PCR reaction.

5) Storage of the buffy coat samples for 24 to 48 hours did not affect the cell counts (WBC/ml, RBC/ml, Platelet/ml) or the phenotypes (% Lymphocytes, % Monocytes, % Granulocytes) as compared to the Day 0 "fresh" buffy coat samples. However, the storage of the buffy coats for 24 or 48 hours did decrease the percentage of lymphocytes in the post syringe chamber samples, collected at 400×g for 10 minutes. The lymphocyte percentage decreased from 83.28% in the fresh syringe chamber sample to 41.42% in the 48 hour sample. After 24 hours the lymphocyte percentage decreased to 60.74% from a Day 0 lymphocyte percentage of 87.7%.

II. Leukocyte Isolation Using Modified Syringe Leukocyte Collection Chamber of FIG. 3

Isolation of leukocytes from high speed buffy coat preparations prepared from 24 hour old blood received from Interstate Blood Bank, using the modified syringe leukocyte collection chamber of FIG. 3.

A total of four high speed (>3500×g) Optipress® device buffy coat preparations were processed using the modified syringe leukocyte collection chambers of FIG. 3. Cell counts were performed using a Sysmex K-1000 automated cell counter on both the pre chamber buffy coats and the post syringe chamber collected samples. Detailed phenotypic analysis was also performed on the pre and post chamber samples to characterize the lymphocyte subpopulations (CD3, CD4, CD8, NK, CD19) along the monocyte and granulocyte populations.

Table 5 summarizes the cell counts of the raw buffy coat pre chamber samples and the post syringe chamber samples collected at different centrifugation forces and times. The mean WBC concentration of the pre chamber samples was 2.615×10$^7$/ml. Post chamber collected samples displayed a decrease in WBC concentration with a decrease in both centrifugation force and time. All the post chamber collected samples contained greater than 1×10$^6$ WBC's used in a typical PCR digestion reaction. Decreasing the time and force of the centrifugation resulted in increased levels of RBC contamination in the post chamber samples. The platelet concentration in the post chamber collected samples was often above the detectable limits of the Sysmex K-1000 cell counter. However, the total number of RBC's and/or platelets that would be present in a 1×10$^6$ WBC sample would not interfere with the PCR reaction. A centrifugation time of either 5 or 7 minutes at 750×g appears to yield the best sample for PCR analysis. These samples gave sufficient WBC numbers (>1×10$^6$) with acceptable levels of RBC's ($\leq$5×10$^8$) and/or platelets ($\leq$5×10$^9$) to be used directly for PCR analysis.

Table 6 summarizes the phenotypes of the post chamber samples. Only a single sample was processed in the chamber at 1500×g for 7 or 10 minutes. In the 1500×g 7 minute post chamber sample the percentage of CD3 (T-lymphocytes), CD4 (T-helper), CD8 (T-suppressor) and CD14 (monocytes) cells increased slightly as compared to the pre chamber percentages. Natural Killer cells (NK, CD16) and B-lymphocytes (CD19) increased from pre chamber percentages of 6.34% and 5.66% to post chamber values of 11.66% and 10.79% respectively. Granulocytes (CD16) decreased from 35.29% to 6.92% after processing of the high speed buffy coat fraction with the syringe chamber at 1500×g for 7 minutes. Increasing the centrifugation time to 10 minutes at 1500×g resulted in post chamber samples having percentages of CD3, CD4, CD8, CD16, CD19, CD14 and CD16 cells similar to the pre chamber buffy coat values.

Optipress® device buffy coat samples were processed in the modified syringe leukocyte collection chambers of FIG. 3 at 1000×g for 5, 7, and 10 minutes. The CD3+T-lymphocyte percentages were increased in the 5 minute sample (mean=41.67%), similar at 7 minutes (mean=34.24) and decreased in the 10 minute samples (17.87%) as compared to the pre chamber samples (mean=34.47%). T-helper (CD4) and T-suppressor (CD8) values were similar to their pre chamber values. CD16+NK cells increased from a pre chamber value of 6.34% to 12.07%, 12.47%, and 17.35% in the 5, 7, and 10 minutes post chamber samples respectively. Samples processed for 5 minutes at 1000×g had a Cr3+ percentage (mean=12.40%) similar to the pre chamber samples percentage (mean 12.79%). Post chamber Cr3+ (NK percentages were increased in the 7 minute (mean= 23.19%) and 10 minute (mean=20.30%) samples. B-lymphocytes increased from 6.23% to 14.26% in the 5 minute, 14.57% in the 7 minute, to 24.85% in the 10 minute post chamber samples (%=mean values). Monocyte percentages were slightly elevated in the 5 and 10 minute samples (pre mean=10.96%: 5 minutes mean =13.17; 10 minutes mean=13.06%) and 1.9× greater in the 7 minute (mean= 20.85%) post chamber sample. The amount of granulocytes (pre chamber mean=38.57%) decreased to 11.30% (mean) in the 5 minute, 25.86% (mean) in the 7 minute, and 19.27% (mean) in the 10 minute post chamber samples centrifuged at 1000×g.

Samples processed at 750×g for 5 minutes had a decrease in the T-lymphocyte number from a pre chamber mean of 34.47% to a post chamber value of 26.85%. T-lymphocyte values in the 7 or 10 minutes post chamber samples gave CD3+ values similar to the pre chamber percentage (7 minutes mean=31.69%; 10 minutes mean=30.05%). An increase in the CD4+, T-helper cells, percentages was not observed in any of three centrifugation times tested. The CD8+, T-suppressor cells, also did not show an enrichment in any of the post chamber samples collected at 750×g for 5, 7, or 10 minutes. NK cells (Cr3+) increased in each of the post chamber samples. Cr3+ NK cells increased 1.4× the pre chamber in the 5 minute samples (pre mean=12.79%; 5 minute mean=18.01%). Also, the Cr3+ percentage in the 7 (mean=25.75%) and 10 (mean=25.40%) minute samples increased >2× the pre chamber mean Cr3+ percentage (mean=12.79%). An enrichment in the B-lymphocyte, CD19+, percentage was observed in all of the post chamber samples collected at 750×g. Monocyte, CD14+, percentages were also greater than the pre chamber percentage for each of the different centrifugation times. The 5 minute post chamber samples had the highest CD14+ percentage 26.76%. Increasing the centrifugation time resulted in a decrease in the CD14+ percent (7 minute mean=20.3.1%; 10 minute mean=14.66%) but were still greater than the pre chamber sample CD14+ percentage. A decrease in granulocyte contamination was observed for all the post chamber samples. The Cr3+ granulocyte percent decreased from a pre chamber value of 38.57% (mean) to 5.16% (mean) in the 5 minute, 7.48% (mean) 7 minute, and 16.50% (mean) in the 10 minute post chamber samples.

Optipress® device buffy coat fractions were also processed in the modified syringe leukocyte collection chamber of FIG. 3 at 500×g for 7 or 10 minutes. No conclusions could be made in the 7 minute sample due incomplete phenotyping results. The CD4+ percentage in this sample (23.35%) was similar to the pre chamber percentage (7-7:I 26.61%). The T-suppressor value was also similar to pre chamber value (Pre=17.33; 7 minute=20.84%). The CD14+ monocyte percentage did increase from a pre chamber value of 7.37% to a post chamber value of 15.05%. No increase in the percentage of CD3+, CD4+, CD8+, CD16+ or Cr3+ (NK) cells were observed in the post syringe chamber samples collected at 500×g for 10 minutes. The B-lymphocyte percentage increased from 6.53% (mean) to 11.51%, while the monocyte percentage increased from 10.96% (mean) to 24.95% (mean). A decrease in the number of Cr3+ granulocytes was observed (pre mean=38.57%; 10 minute mean=12.18%) in the 10 minute post chamber samples.

Conclusions

1) High speed Optipress® device buffy coat fractions processed using the modified syringe leukocyte collection chamber of FIG. 3 had platelet concentrations ($\leq 5 \times 10^9$) and/or RBC concentrations ($\leq 5 \times 10^8$) that would not inhibit PCR reactions ($1 \times 10^6$ WBC/PCR digestion reaction).

2) The total number of WBC's collected from the syringe chambers were sufficient to perform a typical PCR digestion reaction ($1 \times 10^6$ WBC).

3) T-lymphocyte (CD3+) concentrations were not enriched for in the post chamber samples except in the 1000×g 5 minute samples where an increased percentage of CD3+ cells was observed. The CD3+ percentage in the other post syringe chamber collected samples were similar to the CD3+ percentage in the pre chamber high speed Optipress buffy coat fractions.

4) The CD4+ T-helper cell subpopulation was not enriched in the post chamber collected samples at any of the centrifugation forces or times tested. CD8+ T-suppressor cells also were not enriched in the final post chamber samples.

5) Natural Killer cell (Cr3+) percentages were increased in the 7 and 10 minute 1000×g and also all of the 750×g post chamber collected samples.

6) An enrichment in the concentration of B-lymphocytes (CD19+) was observed in all the post chamber collected samples. Decreasing the centrifugation force from 1000×g to 750×g increased the CD19+ percentage in the post chamber samples.

7) Monocytes (CD14+) showed slight increases in their percentages in the 5 and 10 minute 1000×g collected samples. The 1000×g 7 minute samples had a 1.9 fold increase in CD14+ cells over the pre chamber high speed Optipress buffy coat samples. Post chamber samples collected at 750×g also displayed increased CD14+ concentrations as compared to the pre chamber fractions. However, a decrease in the CD14+ percentage was observed with an increase in the centrifugation time at 750×g.

8) Granulocyte contamination (Cr3+) was decreased in all the post chamber collected samples.

9) The optimal centrifugation force required to process a high speed Optipress® device buffy coat fraction in the syringe chamber for PCR testing appears to be 750×g. A centrifugation time of 5–7 minutes appears to be required to collect the best PCR sample.

SUMMARY

The modified syringe leukocyte collection chamber of FIG. 3 offers a convenient method to collect a leukocyte rich sample from a mixed population of blood cells for use in PCR screening of blood for viral contamination. The optimal speed required to collect a PCR sample from either a slow speed (<3000 rpm) or a high speed (>3500 rpm) Optipress® device buffy coat preparation was 750×g. These samples would provide sufficient numbers of WBC's ($1 \times 10^6$) with minimal RBC ($\leq 5 \times 10^8$) and/or platelet ($\leq 5 \times 10^9$) contamination for use directly in the PCR analysis.

However, slow speed Optipress® device buffy coat fractions had a greater percentage of lymphocytes in the post syringe samples (750×g>45%). This increased lymphocyte concentration may increase the sensitivity of PCR analysis for HIV infection. The use of slow speed buffy coat fractions prepared from fresh blood (<4 hours old) may also increase WBC recovery and lymphocyte purity in the post syringe chamber samples. Storage of the buffy coat for 24–48 hours decreases the efficiency of the chamber to collect lymphocyte enriched samples.

In summary, the modified syringe leukocyte collection chamber of FIG. 3 offers a quick and convenient method of collecting leukocyte rich PCR samples using Optipress® device buffy coat preparations.

TABLE 1

Summary of cell counts pre and post processing of slow speed Optipress ® device buffy coat preparations with the Modified Syringe Leukocyte Collection Chamber.

| Sample Id | Time | WBC/ml | RBC/ml | PLT/ml | HCT | mis Sample |
|---|---|---|---|---|---|---|
| \multicolumn{7}{c}{Raw Buffy Coat: Pre Chamber Values} | | | | | | |
| 5-15:A | — | 28,400,000 | 4,300,000,000 | 277,000,000 | 35.9 | — |
| 5-15:C | — | 66,400,000 | 4,450,000,000 | 602,000,000 | 58.6 | — |
| 5-19:A | — | 22,200,000 | 5,420,000,000 | 230,000,000 | 42.9 | — |
| 5-28: | — | 39,000,000 | 3,790,000,000 | 387,000,000 | 38.1 | — |
| 6-2:A | — | 27,700,000 | 4,490,000,000 | 188,000,000 | 42.9 | — |
| 6-2:B | — | 34,000,000 | 4,060,000,000 | 215,000,000 | 40.4 | — |
| 6-2:D | — | 63,800,000 | 3,630,000,000 | 577,000,000 | 39.39 | — |
| 6-2:E | — | 37,700,000 | 4,900,000,000 | 287,000,000 | 41.3 | — |
| | mean | 3.990E+07 | 4.380E+09 | 3.454E+08 | 42.4 | — |
| | Std | 1.544E+07 | 5.464E+08 | 1.518E+08 | 6.5 | — |
| \multicolumn{7}{c}{Post Modified Syringe Leukocyte Collection Chamber: 1000 xg} | | | | | | |
| 5-28: | 5 Minutes | 6,400,000 | 70,000,000 | 540,000,000 | 0.4 | 1.45 |
| 6-2:A | 5 Minutes | 9,000,000 | 100,000,000 | 301,000,000 | 0.7 | 2.10 |
| 6-2:B | 5 Minutes | 9,600,000 | 90,000,000 | 346,000,000 | 0.6 | 2.20 |
| 6-2:D | 5 Minutes | 2,300,000 | 100,000,000 | 932,000,000 | 0.5 | 2.10 |
| 6-2:E | 5 Minutes | 400,000 | 60,000,000 | 547,000,000 | 0.3 | 2.60 |
| | Mean | 5.540E+06 | 8.400E+07 | 5.332E+08 | 0.5 | 2.09 |
| | Std | 3.636E+06 | 1.625E+07 | 2.228E+08 | 0.1 | 0.37 |
| \multicolumn{7}{c}{Post Modified Syringe Leukocyte Collection Chamber: 100 xg} | | | | | | |
| 5-28: | 7 Minutes | 4,200,000 | 60,000,000 | 540,000,000 | 0.4 | 1.45 |
| 6-2:A | 7 Minutes | 2,900,000 | 5,000,000 | 301,000,000 | 0.7 | 2.10 |
| 6-2:B | 7 Minutes | 1,500,000 | 30,000,000 | 346,000,000 | 0.6 | 2.20 |
| 6-2:D | 7 Minutes | 200,000 | 50,000,000 | 932,000,000 | 0.5 | 2.10 |
| 6-2:E | 7 Minutes | 200,000 | 30,000,000 | 547,000,000 | 0.3 | 2.60 |
| | Mean | 1.800E+06 | 3.500E+07 | 4.204E+08 | 0.2 | 2.01 |
| | Std | 1.561E+06 | 1.897E+07 | 1.882E+08 | 0.1 | 0.22 |
| \multicolumn{7}{c}{Post Modified Syringe Leukocyte Collection Chamber: 1000 xg} | | | | | | |
| 5-28: | 10 Minutes | 8,500,000 | 60,000 | 491,000,000 | 0.4 | 1.80 |
| 6-2:A | 10 Minutes | 2,800,000 | 30,000 | 95,000,000 | 0.2 | 1.70 |
| 6-2:B | 10 Minutes | 3,000,000 | 20,000 | 202,000,000 | 0.1 | 1.90 |
| 6-2:D | 10 Minutes | 200,000 | 30,000 | 699,000,000 | 0.1 | 1.90 |
| 6-2:E | 10 Minutes | 1,000,000 | 30,000 | 307,000,000 | 0.1 | 2.10 |
| | Mean | 2.100E+06 | 3.400E+04 | 3.588E+08 | 0.2 | 1.88 |
| | Std | 2.901E+06 | 1.356E+04 | 2.145E+08 | 01 | 0.13 |
| \multicolumn{7}{c}{Raw Buffy Coat: Pre Chamber Values} | | | | | | |
| 5-15:A | — | 28,400,000 | 4,300,000,000 | 277,000,000 | 35.9 | — |
| 5-15:C | — | 66,400,000 | 4,450,000,000 | 602,000,000 | 58.6 | — |
| 5-19:A | — | 22,200,000 | 5,420,000,000 | 230,000,000 | 42.9 | — |
| 5-28: | — | 39,000,000 | 3,790,000,000 | 387,000,000 | 38.1 | — |
| 6-2:A | — | 27,700,000 | 4,490,000,000 | 188,000,000 | 42.9 | — |
| 6-2:B | — | 34,000,000 | 4,060,000,000 | 215,000,000 | 40.4 | — |
| 6-2:D | — | 63,800,000 | 3,630,000,000 | 577,000,000 | 39.3 | — |
| 6-2:E | — | 37,700,000 | 4,900,000,000 | 287,000,000 | 41.3 | — |
| | mean | 3.990E+07 | 4.380E+09 | 3.454E+08 | 42.4 | — |
| | Std | 1.544E+07 | 5.464E+08 | 1.518E+08 | 6.5 | — |
| \multicolumn{7}{c}{Post Modified Syringe Leukocyte Collection Chamber: 750 xg} | | | | | | |
| 5-28: | 5 Minutes | 5,900,000 | 70,000,000 | 653,000,000 | 0.4 | 1.10 |
| 6-2:A | 5 Minutes | 100,000 | 30,000,000 | 392,000,000 | 0.1 | 2.30 |
| 6-2:B | 5 Minutes | 3,100,000 | 70,000,000 | 297,000,000 | 0.3 | 2.20 |
| 6-2:D | 5 Minutes | 1,200,000 | 100,000,000 | 989,000,000 | 0.3 | 2.30 |
| 6-2:E | 5 Minutes | 500,000 | 50,000,000 | 556,000,000 | 0.2 | 2.80 |
| | Mean | 2.160E+06 | 6.400E+07 | 5.774E+08 | 0.3 | 2.14 |
| | Std | 2.135E+06 | 2.332E+07 | 2.402E+08 | 0.1 | 0.56 |
| \multicolumn{7}{c}{Post Modified Syringe Leukocyte Collection Chamber: 750 xg} | | | | | | |
| 5-28: | 7 Minutes | 5,500,000 | 60,000,000 | 586,000,000 | 0.3 | 1.40 |
| 6-2:A | 7 Minutes | 1,000,000 | 30,000,000 | 248,000,000 | 0.1 | 1.90 |
| 6-2:B | 7 Minutes | 500,000 | 30,000,000 | 330,000,000 | 0.1 | 2.40 |
| 6-2:D | 7 Minutes | 1,200,000 | 700,000 | 941,000,000 | 0.2 | 2.10 |

TABLE 1-continued

Summary of cell counts pre and post processing of slow speed Optipress ® device buffy coat preparations with the Modified Syringe Leukocyte Collection Chamber.

| Sample Id | Time | WBC/ml | RBC/ml | PLT/ml | HCT | mis Sample |
|---|---|---|---|---|---|---|
| 6-2:E | 7 Minutes | 300,000 | 50,000,000 | 531,000,000 | 0.2 | 2.50 |
| | Mean | 1.700E+06 | 3.414E+04 | 5.272E+08 | 0.2 | 2.06 |
| | Std | 1.928E+06 | 2.036E+04 | 2.476E+08 | 0.1 | 0.39 |
| Post Modified Syringe Leukocyte Collection Chamber: 750 xg | | | | | | |
| 5-28: | 10 Minutes | 11,000,000 | 30,000 | 447,000,000 | 0.2 | 1.75 |
| 6-2:A | 10 Minutes | 700,000 | 20,000 | 168,000,000 | 0.1 | 1.80 |
| 6-2:B | 10 Minutes | 100,000 | 10,000 | 243,000,000 | 0.0 | 2.10 |
| 6-2:D | 10 Minutes | 3,500,000 | 50,000 | 807,000,000 | 0.2 | 1.90 |
| | Mean | 3.825E+06 | 2.750E+04 | 4.163E+08 | 0.1 | 1.89 |
| | Std | 4.337E+06 | 1.479E+04 | 2.476E+08 | 0.1 | 0.13 |
| Raw Buffy Coat: Pre Chamber Values | | | | | | |
| 5-15:A | — | 28,400,000 | 4,300,000,000 | 277,000,000 | 35.9 | — |
| 5-15:C | — | 66,400,000 | 4,450,000,000 | 602,000,000 | 58.6 | — |
| 5-19:A | — | 22,200,000 | 5,420,000,000 | 230,000,000 | 42.9 | — |
| 5-28: | — | 39,000,000 | 3,790,000,000 | 387,000,000 | 38.1 | — |
| 6-2:A | — | 27,700,000 | 4,490,000,000 | 188,000,000 | 42.9 | — |
| 6-2:B | — | 34,000,000 | 4,060,000,000 | 215,000,000 | 40.4 | — |
| 6-2:D | — | 63,800,000 | 3,630,000,000 | 577,000,000 | 39.3 | — |
| 6-2:E | — | 37,700,000 | 4,900,000,000 | 287,000,000 | 41.3 | — |
| | mean | 3.990E+07 | 4.380E+09 | 3.454E+08 | 42.4 | — |
| | Std | 1.544E+07 | 5.464E+08 | 1.518E+08 | 6.5 | — |
| Post Modified Syringe Leukocyte Collection Chamber: 500 xg | | | | | | |
| 5-28: | 5 Minutes | 10,000,000 | 80,000,000 | 625,000,000 | 0.5 | ND |
| Post Modified Syringe Leukocyte Collection Chamber: 500 xg | | | | | | |
| 5-28: | 7 Minutes | 5,100,000 | 80,000,000 | 616,000,000 | 0.4 | 1.00 |
| 6-2:A | 7 Minutes | 1,300,000 | 60,000,000 | 310,000,000 | 0.2 | 2.10 |
| 6-2:B | 7 Minutes | 5,100,000 | 60,000,000 | 388,000,000 | 0.3 | 2.70 |
| 6-2:D | 7 Minutes | 5,400,000 | 130,000,000 | 1,065,000,000 | 0.5 | 2.40 |
| 6-2:E | 7 Minutes | 200,000 | 50,000,000 | 550,000,000 | 0.2 | 2.70 |
| | Mean | 3.420E+06 | 7.600E+07 | 5.858E+08 | 0.3 | 2.18 |
| | Std | 2.210E+06 | 2.871E+07 | 2.634E+08 | 0.1 | 0.63 |
| Post Modified Syringe Leukocyte Collection Chamber: 500 xg | | | | | | |
| 5-15:A | 10 Minutes | 24,800,000 | 300,000 | 331,000,000 | 2.5 | ND |
| 5-15:C | 10 Minutes | 129,000,000 | 340,000 | 1,282,000,000 | 2.4 | ND |
| 5-15:A | 10 Minutes | 200,000 | 30,000 | 257,000,000 | 0.2 | ND |
| 5-28: | 10 Minutes | 3,300,000 | 60,000 | 556,000,000 | 0.3 | 1.40 |
| 6-2:A | 10 Minutes | 400,000 | 20,000 | 226,000.000 | 0.1 | 2.10 |
| 6-2:B | 10 Minutes | 700,000 | 20,000 | 275,000,000 | 0.1 | 2.30 |
| 6-2:D | 10 Minutes | 3,200,000 | 90,000 | 945,000,000 | 0.3 | 2.00 |
| 6-2:E | 10 Minutes | 600,000 | 50,000 | 503,000,000 | 0.2 | 2.40 |
| | Mean | 2.028E+07 | 1.138E+05 | 5.469E+08 | 0.8 | 2.04 |
| | Std | 4.182E+07 | 1.214E+05 | 3.550E+08 | 1.0 | 0.35 |

TABLE 2

Summary of cell phenotypes pre and post processing of slow speed Optipress ® device buffy coat preparations with the Modified Syringe Leukocyte Collection Chamber.

| Sample Id | Time | Lymphocytes | Monocytes | Granulocytes |
|---|---|---|---|---|
| Raw Buffy Coat: Pre Chamber Values Phenotypes based on light scattering properties (FSC vs. SSC) of the HLe positive cells. | | | | |
| 5-15:A | | 45.63% | 22.07% | 20.85% |
| 5-15:C | | 9.18% | 11.82% | 74.02% |
| 5-19:A | | 14.89% | 5.97% | 76.28% |
| 5-28: | | 39.65% | 8.33% | 47.36% |
| 6-2:A | | 36.34% | 0.67% | 61.28% |
| 6-2:D | | 32.88% | 0.24% | 65.38% |
| 6-2:E | | 61.93% | 0.19% | 36.11% |
| | Mean | 34.36% | 3.18% | 54.47% |
| | Std | 16.62% | 1.20% | 19.05% |
| Post Modified Syringe Leukocyte Collection Chamber: 1000 xg | | | | |
| 5-28: | 5 Minutes | 91.64% | 3.30% | 0.47% |
| 6-2:A | 5 Minutes | 64.90% | 4.18% | 26.35% |
| 6-2:B | 5 Minutes | 85.51% | 2.27% | 10.26% |
| 6-2:D | 5 Minutes | 77.95% | 1.44% | 17.39% |
| 6-2:E | 5 Minutes | 77.96% | 4.70% | 7.65% |
| | Mean | 79.59% | 3.18% | 12.42% |
| | Std | 8.96% | 1.20% | 8.82% |
| Post Modified Syringe Leukocyte Collection Chamber: 1000 xg | | | | |
| 5-28: | 7 Minutes | 81.82% | 13.42% | 0.98% |
| 6-2:A | 7 Minutes | 64.63% | 4.16% | 28.23% |
| 6-2:B | 7 Minutes | 81.55% | 3.71% | 11.73% |
| 6-2:E | 7 Minutes | 57.12% | 7.73% | 13.71% |
| | Mean | 71.28% | 7.25% | 13.66% |
| | Std | 10.74% | 3.89% | 9.71% |
| Post Modified Syringe Leukocyte Collection Chamber: 1000 xg | | | | |
| 5-28: | 10 Minutes | 82.25% | 13.20% | 1.10% |
| 6-2:A | 10 Minutes | 66.05% | 2.46% | 29.30% |
| 6-2:B | 10 Minutes | 68.99% | 2.46% | 25.09% |
| 6-2:E | 10 Minutes | 65.11% | 8.00% | 14.99% |
| | Mean | 70.60% | 6.53% | 17.62% |
| | Std | 6.88% | 4.47% | 10.86% |
| Post Modified Syringe Leukocyte Collection Chamber: 750 xg | | | | |
| 5-28: | 5 Minutes | 94.30% | 2.17% | 0.42% |
| 6-2:B | 5 Minutes | 91.14% | 3.18% | 3.36% |
| 6-2:D | 5 Minutes | 55.68% | 1.14% | 36.92% |
| 6-2:E | 5 Minutes | 82.58% | 2.31% | 6.12% |
| | Mean | 80.93% | 2.20% | 11.71% |
| | Std | 15.19% | 0.72% | 14.70% |
| Post Modified Syringe Leukocyte Collection Chamber: 750 xg | | | | |
| 5-28: | 7 Minutes | 93.00% | 3.70% | 0.35% |
| 6-2:A | 7 Minutes | 78.43% | 2.80% | 15.46% |
| 6-2:B | 7 Minutes | 78.56% | 2.33% | 14.63% |
| 6-2:D | 7 Minutes | 66.45% | 1.50% | 27.26% |
| 6-2:E | 7 Minutes | 78.59% | 3.01% | 7.40% |
| | Mean | 79.01% | 2.67% | 13.02% |
| | Std | 8.42% | 0.73% | 8.98% |
| Post Modified Syringe Leukocyte Collection Chamber: 750 xg | | | | |
| 5-28: | 10 Minutes | 78.05% | 9.04% | 1.55% |
| 6-2:A | 10 Minutes | 69.94% | 2.79% | 22.75% |
| 6-2:B | 10 Minutes | 61.68% | 4.19% | 23.19% |
| 6-2:D | 10 Minutes | 59.86% | 1.12% | 34.50% |
| | Mean | 67.38% | 4.29% | 20.50% |
| | Std | 7.24% | 2.95% | 11.91% |
| Post Modified Syringe Leukocyte Collection Chamber: 750 xg | | | | |
| 5-28: | 5 Minutes | 92.41% | 3.53% | 0.17% |
| Post Modified Syringe Leukocyte Collection Chamber: 500 xg | | | | |
| 5-28: | 7 Minutes | 94.07% | 2.50% | 0.24% |
| 6-2:A | 7 Minutes | 80.86% | 3.78% | 11.67% |
| 6-2:B | 7 Minutes | 75.48% | 2.68% | 17.80% |
| 6-2:D | 7 Minutes | 53.46% | 0.88% | 40.91% |
| 6-2:E | 7 Minutes | 73.39% | 1.73% | 7.81% |
| | Mean | 75.45% | 2.31% | 15.69% |
| | Std | 13.14% | 0.97% | 13.84% |
| Post Modified Syringe Leukocyte Collection Chamber: 500 xg | | | | |
| 5-15:A | 10 Minutes | 33.45% | 32.06% | 28.08% |
| 5-15:C | 10 Minutes | 8.47% | 13.43% | 71.29% |
| 5-28: | 10 Minutes | 92.08% | 3.90% | 0.52% |
| 6-2:A | 10 Minutes | 58.90% | 2.39% | 29.88% |
| 6-2:B | 10 Minutes | 73.01% | 3.36% | 17.41% |
| 6-2:D | 10 Minutes | 61.74% | 1.01% | 33.67% |
| 6-2:E | 10 Minutes | 76.77% | 2.63% | 10.41% |
| | Mean | 57.77% | 8.40% | 27.32% |
| | Std | 26.21% | 10.38% | 20.99% |

TABLE 3a

Summary of the cell counts pre and post processing of Optipress ® device buffy coat prepartion with the modified syringe leukocyte collection chamber.
Fresh Optipress ® device buffy coat prepared from <4 hour old blood

| | | Summary Of Cell Counts w/Sysmex K-1000 | | |
| 10 Minute Centrifugation | | | | |
|---|---|---|---|---|
| Sample Id | WBC/ml | RBC/ml | Plt/ml | HCT |
| Pre (Control) | 38,300,000 | 4,880,000,000 | 318,000,000 | 48.5% |
| 500 xg | 8,800,000 | 100,000,000 | 502,000,000 | 0.6% |
| 400 xg | 6,400,000 | 70,000,000 | 549,000,000 | 0.3% |
| 300 xg | 13,400,000 | 90,000,000 | 371,000,000 | 0.5% |
| 200 xg | 23,600,000 | 120,000,000 | 547,000,000 | 0.8% |
| 100 xg | 81,000,000 | 200,000,000 | 469,000,000 | 1.8% |

TABLE 3b

Summary of the cell counts pre and post processing of Optipress ® device buffy coat prepartion with the modified syringe leukocyte collection chamber.
48 hour old Optipress ® device buffy coat stored at room temperature

| | | Summary Of Cell Counts w/Sysmex K-1000 | | |
| 10 Minute Centrifugation | | | | |
|---|---|---|---|---|
| Sample Id | WBC/ml | RBC/ml | Plt/ml | HCT |
| Pre (Control) | 35,400,000 | 5,000,000,000 | 309,000,000 | 53.8% |
| 400 xg #1 | 37,300,000 | 190,000,000 | 509,000,000 | 1.5% |
| 400 xg #2 | 42,300,000 | 160,000,000 | 503,000,000 | 1.2% |

TABLE 4

Summary of the cell counts pre and post processing of Optipress ® device buffy coat prepartion with the modified syringe leukocyte collection chamber.
Fresh Optipress ® device buffy coat prepared from <4 hour old blood

| | | Summary Of Cell Counts w/Sysmex K-1000 | | |
| 10 Minute Centrifugation | | | | |
|---|---|---|---|---|
| Sample Id | WBC/ml | RBC/ml | Plt/ml | HCT |
| Pre (Control) | 28,100,000 | 4,760,000,000 | 275,000,000 | 43.9% |
| 500 xg #1 | 4,700,000 | 60,000,000 | 381,000,000 | 0.3% |
| 500 xg #2 | 6,100,000 | 70,000,000 | 447,000,000 | 0.4% |
| 400 xg #1 | 14,300,000 | 100,000,000 | 539,000,000 | 0.5% |
| 400 xg #2 | 8,700,000 | 80,000,000 | 526,000,000 | 0.4% |

TABLE 4-continued

Summary of the cell counts pre and post processing of
Optipress ® device buffy coat prepartion with the modified
syringe leukocyte collection chamber.
Fresh Optipress ® device buffy coat prepared from <4 hour old blood

| 10 Minute Centrifugation | | Summary Of Cell Counts w/Sysmex K-1000 | | |
|---|---|---|---|---|
| Sample Id | WBC/ml | RBC/ml | Plt/ml | HCT |
| 300 xg #1 | 5,900,000 | 80,000,000 | 529,000,000 | 0.4% |
| 300 xg #2 | 12,400,000 | 90,000,000 | 541,000,000 | 0.5% |
| 200 xg #1 | 15,600,000 | 90,000,000 | 473,000,000 | 0.5% |
| 200 xg #2 | 17,600,000 | 90,000,000 | 475,000,000 | 0.6% |

TABLE 5

Summary of cell counts pre and post processing of high speed Optipress ®
device buffy coat preparations with the Modified Syringe Leukocyte Collection
Chamber.

| Sample Id | Time | WBC/ml | RBC/ml | PLT/ml | HCT | mis Sample |
|---|---|---|---|---|---|---|
| Raw Buffy Coat: Pre Chamber Values | | | | | | |
| 7-7:1 | — | 22,300,000 | 6,130,000,000 | 1,644,000,000 | 62.3 | — |
| 7-28:A | — | 30,200,000 | 4,850,000,000 | 1,506,000,000 | 56.2 | — |
| 7-28:B | — | 38,600,000 | 5,250,000,000 | 1,927,000,000 | 57.9 | — |
| 8-11 | — | 13,500,000 | 7,200,000,000 | 573,000,000 | 69.6 | — |
| | Mean | 2.615E+07 | 5.858E+09 | 1.413E+09 | 61.5 | — |
| | Std | 9.304E+06 | 9.029E+08 | 5.079E+08 | 5.18 | — |
| Post Modified Syringe Leukocyte Collection Chamber: 1500 xg | | | | | | |
| 7-7:1 | 7 Minutes | 10,100,000 | 260,000,000 | ** | 1.3 | 0.75 |
| Post Modified Syringe Leukocyte Collection Chamber: 1500 xg | | | | | | |
| 7-7:1 | 10 Minute | 7,200,000 | 220,000,000 | ** | 1.1 | 0.8 |
| Post Modified Syringe Leukocyte Collection Chamber: 1000 xg | | | | | | |
| 7-7:1 | 5 Minutes | 53,600,000 | 690,000,000 | ** | 5.1 | 0.40 |
| 7-28:A | 5 Minutes | 41,200,000 | 340,000,000 | ** | 3.0 | 0.56 |
| 7-28:B | 5 Minutes | 67,400,000 | 480,000,000 | ** | 2.8 | 0.30 |
| | Mean | 5.407E+07 | 5.033E+08 | ** | 3.63 | 0.45 |
| | Std | 1.070E+07 | 1.438E+08 | ** | 1.04 | 0.15 |
| Post Modified Syringe Leukocyte Collection Chamber: 1000 xg | | | | | | |
| 7-7:1 | 7 Minutes | 6,700,000 | 30,000,000 | 467,000,000 | 0.1 | 0.40 |
| 7-28:A | 7 Minutes | 30,500,000 | 310,000,000 | ** | 2.9 | 0.81 |
| 7-28:B | 7 Minutes | 74,400,000 | 680,000,000 | ** | 4.0 | 0.40 |
| 8-11: | 7 Minutes | 5,700,000 | 390,000,000 | 2,367,000,000 | 1.8 | 0.65 |
| | Mean | 3.687E+07 | 4.600E+08 | ** | 2.90 | 0.62 |
| | Std | 2.841E+07 | 1.590E+08 | ** | 0.90 | 0.17 |
| Post Modified Syringe Leukocyte Collection Chamber: 1000 xg | | | | | | |
| 7-7:1 | 10 Minute | 29,400,000 | 330,000,000 | ** | 2.7 | 0.55 |
| 7-28:A | 10 Minute | 20,800,000 | 290,000,000 | ** | 1.4 | 0.85 |
| 7-28:B | 10 Minute | 34,600,000 | 620,000,000 | ** | 3.2 | 0.50 |
| 8-11: | 10 Minute | 5,100,000 | 300,000,000 | 1,662,000,000 | 2.1 | 0.60 |
| | Mean | 2.248E+07 | 3.850E+08 | ** | 2.35 | 0.63 |
| | Std | 1.118E+07 | 1.365E+08 | ** | 0.67 | 0.13 |

TABLE 5

Summary of cell counts pre and post processing of high speed Optipress ® device buffy coat preparations with the Modified Syringe Leukocyte Collection Chamber.

| Sample Id | Time | WBC/ml | RBC/ml | PLT/ml | HCT | mis Sample |
|---|---|---|---|---|---|---|
| Post Modified Syringe Leukocyte Collection Chamber: 750 xg | | | | | | |
| 7-28:A | 5 Minutes | 34,100,000 | 290,000,000 | ** | 1.7 | 0.50 |
| 7-28:B | 5 Minutes | 58,600.000 | 480,000,000 | 3,412,000,000 | 2.4 | 0.30 |
| | Mean | 4.635E+07 | 3.850E+08 | ** | 2.05 | 0.40 |
| | Std | 1.225E+07 | 9.500E+07 | ** | 0.35 | 0.10 |
| Post Modified syringe Leukocyte Collection Chamber: 750 xg | | | | | | |
| 7-7:1 | 7 Minutes | 20,900,000 | 60,000,000 | 985,000,000 | 0.3 | 0.35 |
| 7-28:A | 7 Minutes | 39,100,000 | 310,000,000 | ** | 3.1 | 0.65 |
| 7-28:B | 7 Minutes | 47,600,000 | 420,000,000 | 2,648,000,000 | 2.2 | 0.40 |
| 8-11: | 7 Minutes | 1,800,000 | 390,000,000 | 2,181,000,000 | 2.9 | 0.57 |
| | Mean | 2.735E+07 | 2.950E+08 | ** | 2.13 | 0.49 |
| | Std | 1.762E+07 | 1.415E+08 | ** | 1.11 | 0.12 |
| Post Modified Syringe Leukocyte Collection Chamber: 750 xg | | | | | | |
| 7-7:1 | 10 Minute | 5,900,000 | 30,000,000 | 615,000,000 | 0.1 | 0.37 |
| 7-28:A | 10 Minute | 32,900,000 | 330,000,000 | ** | 3.0 | 0.80 |
| 7-28:B | 10 Minute | 34,800,000 | 440,000,000 | 2,778,000,000 | 2.2 | 0.50 |
| 8-11: | 10 Minute | 3,000,000 | 20,000,000 | 278,000,000 | 0.1 | 0.51 |
| | Mean | 1.915E+07 | 2.050E+08 | ** | 1.35 | 0.55 |
| | Std | 1.475E+07 | 1.842E+08 | ** | 1.28 | 0.16 |
| Post Modified Syringe Leukocyte Collection Chamber: 500 xg | | | | | | |
| 7-7:1 | 7 Minutes | 4,200,000 | 60,000,000 | 687,000,000 | 0.3 | 0.35 |
| Post Modified Syringe Leukocyte Collection Chamber: 500 xg | | | | | | |
| 7-7:1 | 10 Minute | 4,900,000 | 30,000,000 | 770,000,000 | 0.1 | 0.37 |
| 7-28:A | 10 Minute | 34,000,000 | 360,000,000 | ** | 1.7 | 0.90 |
| 7-28:B | 10 Minute | 52,800,000 | 5,800,000 | ** | 3.2 | 0.40 |
| | Mean | 3.057E+07 | 1.319E+08 | ** | 1.67 | 0.56 |
| | Std | 1.971E+07 | 1.616E+08 | ** | 1.27 | 0.24 |
| Post Modified Syringe Leukocyte Collection Chamber: 400 xg | | | | | | |
| 7-7:1 | 10 Minute | 500,000 | 10,000,000 | 229,000,000 | 0.1 | 0.20 |

TABLE 6

Summary of phenotyping results pre and post processing of high speed Optipress ® device buffy coat preparations with the modified syringe leukocyte collection chamber.

| | Raw Buffy Coat: Pre Chamber Values | | | | Phenotype of cells expressed % MAb + per HLe + cells. | | |
|---|---|---|---|---|---|---|---|
| Sample ID | Time | CD3 | CD4 | Lymphocyte CD8 | CD16 | Cr3 | CD19 |
| 7-7:1 | | 41.10% | 26.61% | 17.33% | 6.34% | — | 5.66% |
| 7-28:A | | 32.01% | 19.46% | 19.07% | — | 14.16% | 6.78% |
| 7-28:B | | 36.00% | 22.65% | 11.61% | — | 6.82% | 8.40% |
| 8:11 | | 28.77% | 17.97% | 14.87% | — | 23.82% | 4.07% |
| | Mean | 34.47% | 21.67% | 15.72% | 6.34% | 11.20% | 6.23% |
| | Std | 4.61% | 3.31% | 2.80% | NA | 8.84% | 1.58% |

| | Raw Buffy Coat: Pre Chamber Values | Phenotype of cells expressed % per MAb + HLe + cells. | |
|---|---|---|---|
| Sample ID | Time | Monocytes CD14 | Granulocytes CD16 | Granulocytes Cr3 |
| 7-7:1 | | 7.37% | 35.29% | — |
| 7-28:A | | 10.25% | — | 41.01% |
| 7-28:B | | 17.43% | — | 48.16% |
| 8-11 | | 8.77% | — | 26.55% |
| | Mean | 10.96% | 35.29% | 38.57% |
| | Std | 3.87% | NA | 16.43% |

| | Post Modified Syringe Collection Chamber: 1500 xg | | | Phenotype af cells expressed % MAb + per HLe + cells | | | |
|---|---|---|---|---|---|---|---|
| Sample ID | Time | CD3 | CD4 | Lymphocyte CD8 | CD16 | Cr3 | CD19 |
| 7-7:1 | 7 Minutes | 52.78% | 34.69% | 23.09% | 11.66% | — | 10.79% |

| | Post Modified Syringe Collection Chamber: 1500 xg | Phenotype af cells expressed % MAb + per HLe + cells | |
|---|---|---|---|
| Sample ID | Time | Monocyles CD14 | Granulocytes CD16 | Granulocytes Cr3 |
| 7-7:1 | 7 Minutes | 10.89% | 6.92% | — |

TABLE 6-continued

Summary of phenotyping results pre and post processing of high speed Optipress ® device buffy coat preparations with the modified syringe leukocyte collection chamber.

Post Modified Syringe Collection Chamber: 1500 xg
Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 10 Minutes | 39.74% | 27.22% | 18.12% | 8.09% | — | 7.29% |

Post Modified Syringe Collection Chamber: 1500 xg
Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 10 Minutes | 8.33% | 30.14 | — |

Post Modified Syringe Collection Chamber: 1000 xg
Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 5 Min. | 51.99% | 32.65% | 22.90% | 12.07% | — | 10.03% |
| 7-28:B | 5 Min. | 31.34% | 18.65% | 9.84% | — | 12.73% | 15.54% |
| 7-28:A | 5 Min. | LS | 21.52% | 22.00% | — | 12.07% | 17.20% |
| | Mean | 41.67% | 24.27% | 18.25% | 12.07% | 12.40% | 14.26% |
| | Std | 10.33% | 6.04% | 13.37% | NA | 6.65% | 3.06% |

Post Modified Syringe Collection Chamber: 1000 xg
Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 5 Minutes | 11.83% | 13.19% | — |
| 7-28:B | 5 Minutes | LS | — | 5.88% |
| 7-28:A | 5 Minutes | 14.51% | — | 16.72% |
| | Mean | 13.17% | 13.19% | 11.30% |
| | Std | 1.34% | NA | 5.42% |

Post Modified Syringe Collection Chamber: 1000 xg
Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 7 Min. | 44.39% | 25.23% | 18.47% | 12.47% | — | 10.86% |
| 7-28:B | 7 Min. | 26.27% | 16.26% | 18.24% | — | 22.47% | 24.77% |
| 7-28:A | 7 Min. | 36.92% | 21.61% | 12.23% | — | 17.71% | 16.68% |
| 8-11 | 7 Min. | 29.37% | 18.93% | 22.09% | — | 29.40% | 5.95% |
| | Mean | 34.24% | 20.51% | 17.76% | 12.47% | 23.19% | 14.57% |
| | Std | 7.03% | 3.32% | 3.54% | NA | 4.80% | 7.01% |

Post Modified Syringe Collection Chamber: 1000 xg
Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 7 Minutes | 24.73% | 4.89% | — |
| 7-28:B | 7 Minutes | 20.40% | — | 17.19% |
| 7-28:A | 7 Minutes | 27.27% | — | 31.27% |
| 8-11 | 7 Minutes | 11.00% | — | 29.12% |
| | Mean | 20.85% | 4.89% | 26.86% |
| | Std | 6.19% | NA | 6.19% |

Post Modified Syringe Collection Chamber: 1000 xg
Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 10 Min | 7.58% | 25.23% | 19.43% | 17.35% | — | 21.07% |
| 7-28:A | 10 Min | 11.53% | 5.20% | 13.98% | — | 22.34% | 45.79% |
| 7-28:B | 10 Min | 24.22% | 21.58% | 12.55% | — | 7.31% | 22.19% |
| 8-11 | 10 Min | 28.14% | 19.82% | 22.34% | — | 31.25% | 10.34% |
| | Mean | 17.87% | 18.71% | 17.08% | 17.35% | 20.30% | 24.85% |
| | Std | 8.54% | 5.37% | 3.98% | NA | 9.88% | 12.95% |

Post Modified Syringe Collection Chamber: 1000 xg
Phenotype of cells expressed % MAb + per HLe + cells

| Sample ID | Time | Monocytes CD14 | Granulocytes CD16 | Granulocytes Cr3 |
|---|---|---|---|---|
| 7-7:1 | 10 Minutes | 7.07% | 6.63% | — |
| 7-28:A | 10 Minutes | 4.02% | — | 8.57% |
| 7-28:B | 10 Minutes | 28.69% | — | 23.10% |
| 8-11 | 10 Minutes | 12.45% | — | 26.13% |
| | Mean | 13.06% | 6.63% | 19.27% |
| | Std | 9.52% | NA | 7.66% |

Post Modified Syringe Collection Chamber: 750 xg
Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-28:A | 5 Min. | 31.32% | 20.42% | 20.16% | — | 22.59% | 28.08% |
| 7-28:B | 5 Min. | 22.37% | 15.15% | 9.34% | — | 13.43% | 12.29% |
| | Mean | 26.85% | 17.79% | 14.75% | 0.00% | 18.01% | 20.19% |
| | Std | 4.48% | 2.64% | 5.41% | NA | 4.58% | 7.90% |

Post Modified Syringe Collection Chamber: 750 xg
Phenotype of cells expressed % MAb + per HLe + cells

| Sample ID | Time | Monocytes CD14 | Granulocytes CD16 | Granulocytes Cr3 |
|---|---|---|---|---|
| 7-28:A | 5 Minutes | 15.18% | — | 1.11% |
| 7-28:B | 5 Minutes | 38.33% | — | 9.20% |
| | Mean | 26.76% | 0.00% | 5.16% |
| | Std | 11.58% | NA | 4.05% |

Post Modified Syringe Collection Chamber: 750 xg
Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 7 Min. | 51.86% | 25.80% | 23.08% | LS | — | 10.33% |
| 7-28:A | 7 Min. | 25.42% | 14.62% | 15.19% | — | 20.64% | LS |

TABLE 6-continued

Summary of phenotyping results pre and post processing of high speed Optipress ® device buffy coat preparations with the modified syringe leukocyte collection chamber.

| | | | | | | | |
|---|---|---|---|---|---|---|---|
| 7-28:B | 7 Min. | 24.71% | 14.00% | 9.60% | — | 16.82% | 18.76% |
| 8-11 | 7 Min. | 24.77% | 14.48% | 21.18% | — | 39.78% | 11.15% |
| | Mean | 31.69% | 17.23% | 17.26% | — | 25.75% | 13.41% |
| | Std | 11.65% | 4.96% | 5.30% | NA | 10.04% | 3.80% |

Post Modified Syringe Collection Chamber: 750 xg — Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 7 Minutes | 21.10% | LS | — |
| 7-28:B | 7 Minutes | 10.22% | — | 5.29% |
| 7-28:A | 7 Minutes | 36.47% | — | 6.70% |
| 8-11 | 7 Minutes | 13.44% | — | 10.44% |
| | Mean | 20.31% | — | 7.48% |
| | Std | 10.13% | NA | 2.17% |

Post Modified Syringe Collection Chamber: 750 xg — Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 10 Min | 50.07% | 26.74% | 22.64% | 14.67% | — | 13.31% |
| 7-28:A | 10 Min | 26.21% | 6.22% | 16.48% | — | 11.60% | 10.12% |
| 7-28:B | 10 Min | 23.06% | 14.42% | 7.17% | — | 22.44% | 52.87% |
| 8-11 | 10 Min | 20.85% | 15.26% | 25.60% | — | 42.16% | 11.52% |
| | Mean | 30.05% | 15.66% | 17.97% | 14.67% | 25.40% | 21.96% |
| | Std | 11.72% | 7.31% | 7.05% | NA | 12.65% | 17.88% |

Post Modified Syringe Collection Chamber: 750 xg — Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 10 Minutes | 19.05% | 4.48% | — |
| 7-28:A | 10 Minutes | 9.19% | — | 37.16% |
| 7-28:B | 10 Minutes | 7.32% | — | 3.75% |
| 8-11 | 10 Minutes | 23.06% | — | 8.60% |
| | Mean | 14.66% | 448% | 16.50% |
| | Std | 6.59% | NA | 14.74% |

Post Modified Syringe Collection Chamber: 500 xg — Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 7 Min. | LS | 23.35% | 20.84% | LS | — | LS |

Post Modified Syringe Collection Chamber: 500 xg — Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 7 Minutes | 15.05% | LS | — |

TABLE 6-continued

Summary of phenotyping results pre and post processing of high speed Optipress ® device buffy coat preparations with the modified syringe leukocyte collection chamber.

Post Modified Syringe Collection Chamber: 500 xg — Phenotype of cells expressed % MAb + per HLe + cells

| Sample ID | Time | CD3 | CD4 | Lymphocyte CD8 | CD16 | Cr3 | CD19 |
|---|---|---|---|---|---|---|---|
| 7-7:1 | 10 Min | 38.17% | 22.88% | 18.66% | 9.85% | — | 9.02% |
| 7-28:A | 10 Min | 29.98% | 16.53% | 19.07% | — | 19.05% | 13.65% |
| 7-28:B | 10 Min | 25.02% | 13.74% | 12.81% | — | 11.94% | 11.87% |
| | Mean | 31.06% | 17.72% | 16.85% | 9.85% | 16.50% | 11.51% |
| | Std | 5.42% | 3.82% | 2.86% | NA | 3.56% | 1.91% |

Post Modified Syringe Collection Chamber: 500 xg — Phenotype of cells expressed % MAb + per HLe + cells

| Sample ID | Time | Monocyles CD14 | Granulocytes CD16 | Granulocytes Cr3 |
|---|---|---|---|---|
| 7-7:1 | 10 Minutes | 25.93% | 13.54% | — |
| 7-28:A | 10 Minutes | 12.63% | — | 14.06% |
| 7-28:B | 10 Minutes | 36.28% | — | 10.30% |
| | Mean | 24.95% | 13.54% | 12.18% |
| | Std | 9.68% | NA | 1.88% |

Figure 11:
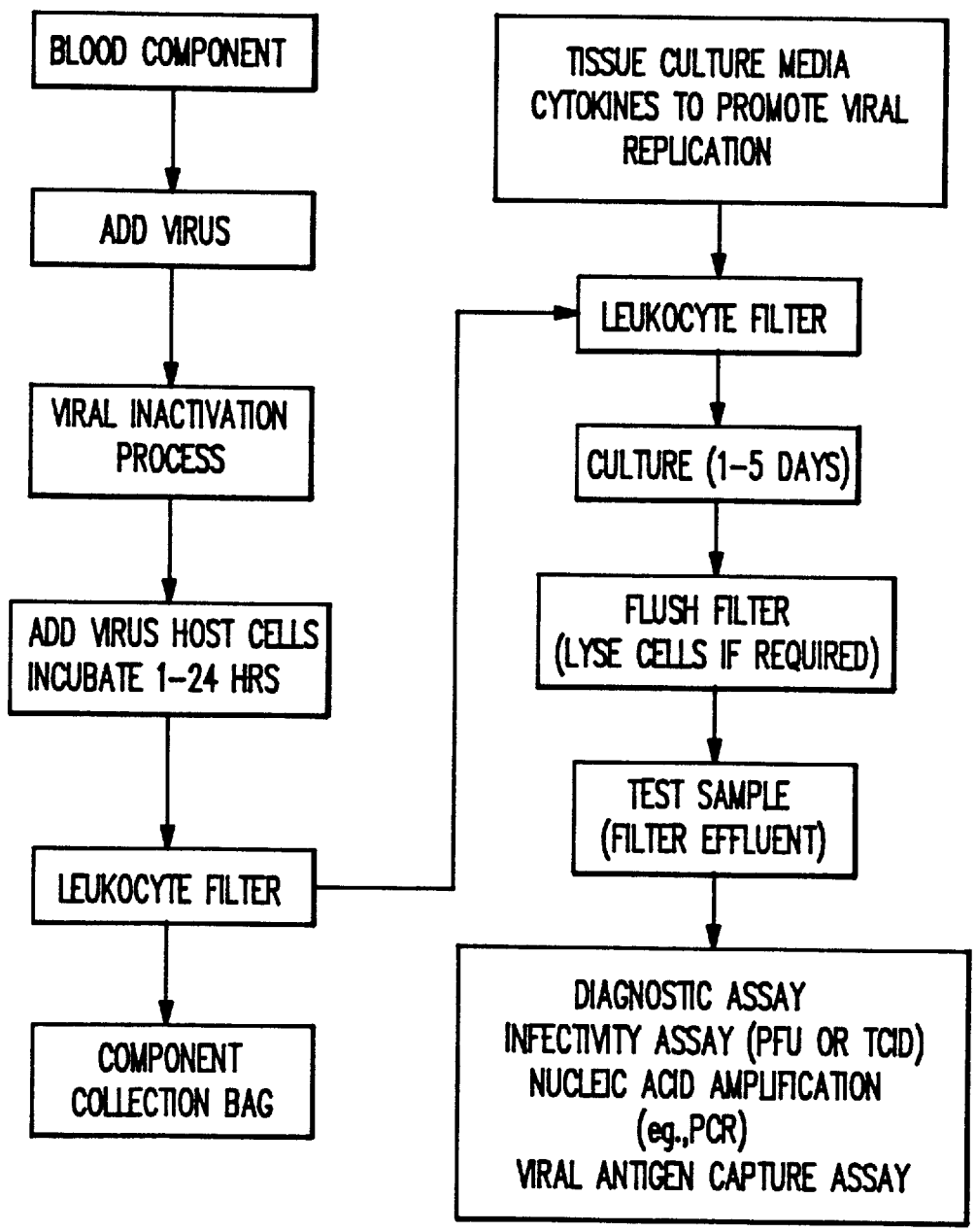
FIG. 11 illustrates schematically the use of an embodiment of the present invention for validating virus depletion/inactivation process.

FIG. 11 illustrates schematically another embodiment of the present invention that can be used for purposes of validating virus depletion/inactivation processes. The method consists of adding virus (e.g., HIV) to a blood component and then treating the blood with a viral inactivation/removal process. Of course, naturally infected blood can be used if desired.

Next, virus host cells are added to the blood (e.g., H9 cells for HIV or Vero cells for VSV). The cells are allowed to incubate in the whole volume of the blood component. During this incubation step, that will last from 1 to 18 hours, infectious virus present in the blood component attach to and penetrate the host cells to initiate the infection process.

In a further step, pursuant to the present invention, the virus host cells are harvested and separated from the blood cells by use of a leukocyte filter. The filter removes cell lines used for viral infectivity studies. Additionally, the filter will remove and separate the leukocytes from platelets and red cells.

The filter is then washed with tissue culture media, such as 10% Fetal Calf Serum in RPMI 1640 media, as required to support the viral host cells. The filter is then incubated at 37° C. for 6–120 hours to allow a virus to continue propagating in the host cells contained in the filter.

At the end of the incubation period, an effluent is prepared from the filter (with or without lysing the host cells) to be used as the test material. The effluent is prepared by flushing the filter with a lysis buffer such as 1% Triton X-100 (Sigma Chemical Co.); 10 mM Tris-HCL, pH 7.0; 1 mM EDTA or a hypotonic solution that lysis the leukocytes but does not inactivate the virus.

The test material is then either tested for infectious virus using conventional tissue culture infectivity assays (e.g., plaque-forming units) or for viral nucleic acid markers (e.g., HIV-DNA sequences using PCR) or viral antigens (e.g., HIV p24 antigen).

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A system for obtaining a leukocyte rich layer comprising:
   a body defining a chamber having a first opening and a second opening, the second opening being defined at least in part by a first outwardly extending flange;
   a plunger having a diameter, including a second outwardly extending flange, received in the second opening for axial movement into and out of the chamber between an opened and a closed positions,
   wherein the opened position corresponds to a maximum allowed distance between the first and second outwardly extending flanges and the closed position corresponds to a minimum allowed distance between the first and second outwardly extending flanges; and
   a removable sleeve comprising a flexibly resilient tubular member having a length and first and second sides, the sleeve further comprising two opposing lips that define an elongated slit extending along the entire length of the sleeve, the lips being biased toward each other so that the slit is substantially narrower than the diameter of the plunger when the sleeve is in a relaxed position, the lips further being manually separable so that the split can be widened to a point where the slit is wider than the diameter of the plunger thereby permitting the sleeve to be opened to receive the plunger and subsequently closed to the relaxed position so that the sleeve substantially surrounds a portion of the plunger disposed between the first and the second outwardly extended flanges, the slit being sufficiently narrow in the relaxed position so as to prevent the plunger being press fit into the sleeve without manually separating the lips prior to receiving the plunger through the lips and into the sleeve,
   wherein the sleeve prevents further axial movement of the plunger into the chamber when the sleeve is coupled around only the portion of the plunger located between the first and second outwardly extending flanges and is pressed between the first and second outwardly extending flanges so that the first side of the sleeve is in contact with the first outwardly extending flange and the second side of the sleeve is in contact with the second outwardly extending flange, and
   wherein the length of the sleeve is closer to the distance between the first and second outwardly extending flanges when the plunger is in the opened position than to the distance between the first and second outwardly extending flanges when the plunger is in the closed position.

* * * * *